US009250134B2

(12) United States Patent
Shepard et al.

(10) Patent No.: US 9,250,134 B2
(45) Date of Patent: Feb. 2, 2016

(54) NONDESTRUCTIVE TESTING ACTIVE THERMOGRAPHY SYSTEM AND METHOD FOR UTILIZING THE SAME

(71) Applicant: THERMAL WAVE IMAGING, INC., Ferndale, MI (US)

(72) Inventors: Steven M. Shepard, Southfield, MI (US); Timothy Young, Oak Park, MI (US); Maria Frendberg Beemer, Clarkston, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 0 days.

(21) Appl. No.: 14/494,298

(22) Filed: Sep. 23, 2014

(65) Prior Publication Data

US 2015/0083920 A1    Mar. 26, 2015

Related U.S. Application Data

(60) Provisional application No. 61/881,278, filed on Sep. 23, 2013.

(51) Int. Cl.
*G01J 5/02* (2006.01)
*G01J 5/08* (2006.01)
*G01N 25/72* (2006.01)
*G01J 5/04* (2006.01)
*G01J 5/00* (2006.01)

(52) U.S. Cl.
CPC ............... *G01J 5/0205* (2013.01); *G01J 5/047* (2013.01); *G01J 5/084* (2013.01); *G01J 5/0809* (2013.01); *G01J 5/0896* (2013.01); *G01N 25/72* (2013.01); *G01J 2005/0081* (2013.01)

(58) Field of Classification Search
CPC ............. G01J 5/02; G01J 5/08; G01J 5/0205; G01J 5/0896
See application file for complete search history.

(56) References Cited

U.S. PATENT DOCUMENTS 5,683,181 A * 11/1997 Shepard .................... G01J 5/02
374/126

(Continued)

*Primary Examiner* — David Porta
*Assistant Examiner* — Faye Boosalis
(74) *Attorney, Agent, or Firm* — Honigman Miller Schwartz and Cohn LLP

(57) ABSTRACT

An assembly including an optically excited infrared nondestructive testing active thermography system is disclosed. The optically excited infrared nondestructive testing active thermography system includes one or more illumination sources, at least one first reflector, at least one second reflector and a computing resource. The at least one first reflector is arranged about the one or more illumination sources. The at least one first reflector has a near focal point and a far focal point. The one or more illumination sources is/are positioned at least proximate the near focal point of the at least one first reflector. The at least one second reflector is positioned at least proximate the far focal point. The computing resource is communicatively-coupled to a motor that is coupled to the at least one second reflector for manipulating the at least one second reflector between at least: a first spatial orientation and a second spatial orientation. At least one of the first spatial orientation and the second spatial orientation results in the at least one second reflector reflecting light that originates from the one or more illumination sources. The light is directed toward the at least one second reflector as a result of the light being directly propagated from the one or more illumination sources and reflected by the at least one first reflector. A method is also disclosed.

82 Claims, 17 Drawing Sheets

(56) References Cited

U.S. PATENT DOCUMENTS 6,751,342 B2 * 6/2004 Shepard .................. G01N 25/72 250/332

6,853,926 B2 * 2/2005 Alfano ................... G01N 21/88 250/339.1

2008/0291465 A1 * 11/2008 Lorraine ............ G01N 21/1717 356/502

* cited by examiner

NONDESTRUCTIVE TESTING ACTIVE THERMOGRAPHY SYSTEM AND METHOD FOR UTILIZING THE SAME

CROSS-REFERENCE TO RELATED APPLICATIONS

This U.S. patent application claims priority to U.S. Provisional Application 61/881,278 filed on Sep. 23, 2013 the disclosure of which is considered part of the disclosure of this application and is hereby incorporated by reference in its entirety.

FIELD OF THE INVENTION

The disclosure relates to a nondestructive testing active thermography system and method for utilizing the same.

DESCRIPTION OF THE RELATED ART

Imaging systems are known in the art. Improvements to imaging systems are continuously being sought in order to advance the arts.

BRIEF DESCRIPTION OF THE DRAWINGS

The disclosure will now be described, by way of example, with reference to the accompanying drawings, in which.

SUMMARY

Figure 1A:
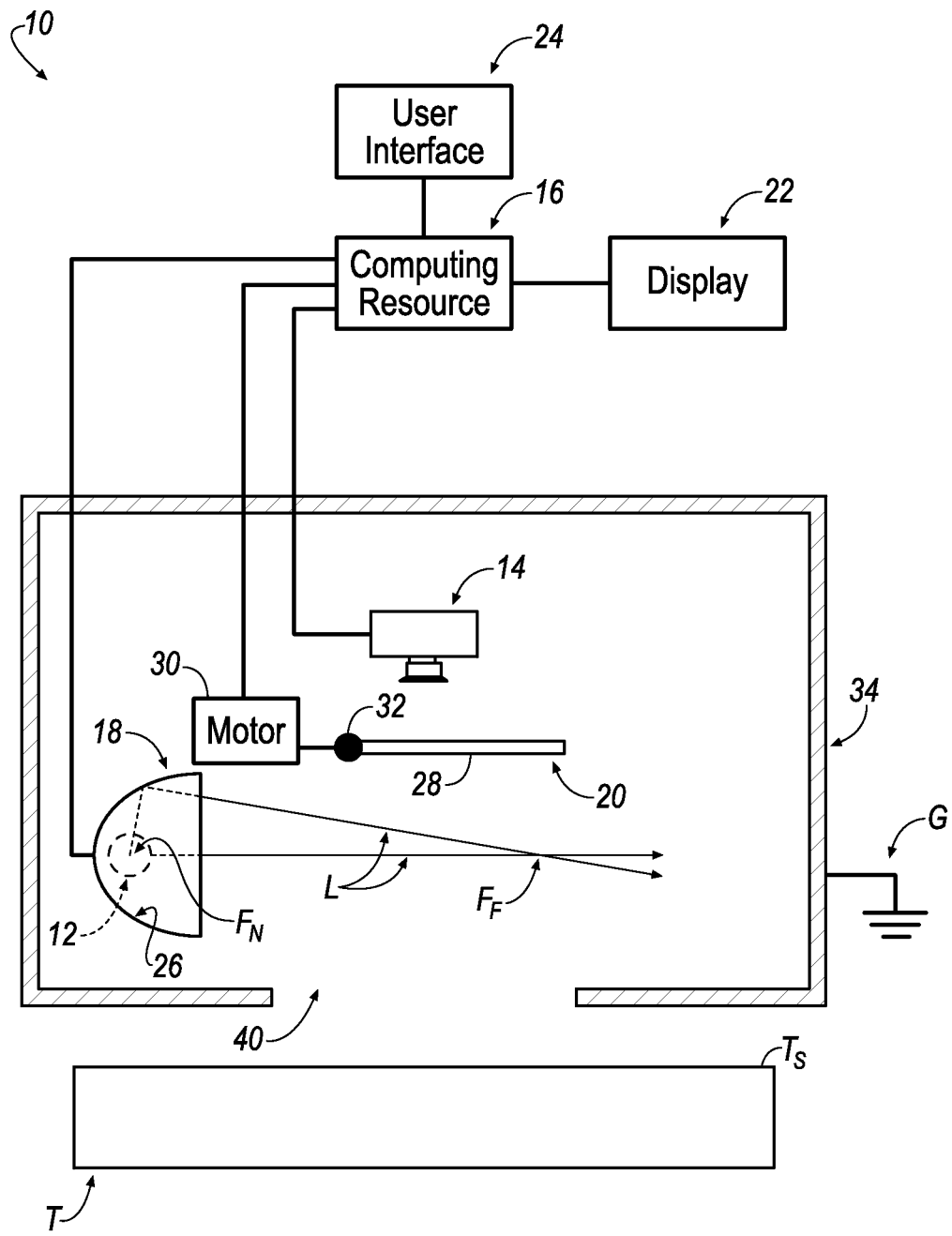
FIG. 1A is a view of an exemplary optically excited infrared (OEIR) nondestructive testing (NDT) active thermography system in accordance with an exemplary embodiment of the invention.

One aspect of the disclosure provides an assembly including an optically excited infrared nondestructive testing active thermography system. The optically excited infrared nondestructive testing active thermography system includes one or more illumination sources, at least one first reflector, at least one second reflector and a computing resource. The at least one first reflector is arranged about the one or more illumination sources. The at least one first reflector has a near focal point and a far focal point. The one or more illumination sources is/are positioned at least proximate the near focal point of the at least one first reflector. The at least one second reflector is positioned at least proximate the far focal point. The computing resource is communicatively-coupled to a motor that is coupled to the at least one second reflector for manipulating the at least one second reflector between at least: a first spatial orientation and a second spatial orientation. The at least one of the first spatial orientation and the second spatial orientation results in the at least one second reflector reflecting light that originates from the one or more illumination sources. The light is directed toward the at least one second reflector as a result of the light being: directly propagated from the one or more illumination sources and reflected by the at least one first reflector.

In some implementations, the system also includes an infrared camera communicatively-coupled to the computing resource. Positioning of the at least one second reflector in the first spatial orientation results in the light being substantially directly and indirectly blocked by the at least one second reflector such that the light is not incident upon or detected by the infrared camera while the light is reflected by the at least one second reflector toward a surface of a test piece.

In some examples, positioning of the at least one second reflector in the second spatial orientation results in the infrared camera detecting heat from the surface of the test piece that was heated as a result of the light that was reflected by the at least one second reflector toward the surface of the test piece while heat emanating from one or more of the one or more illumination sources and the at least one first reflector is blocked by the at least one second reflector such that the heat emanating from one or more of the one or more illumination sources and the at least one first reflector is not incident upon or detected by the infrared camera.

In some instances, the assembly may also include a support structure that is connected to and supports one or more of: the one or more illumination sources, the infrared camera, the at least one first reflector, the at least one second reflector, the computing resource and the motor. The support structure includes a housing portion that is connected to and supports one or more of: the one or more illumination sources, the infrared camera, the at least one first reflector, the at least one second reflector, the computing resource and the motor. The housing portion includes a plurality of interior walls and a plurality of exterior walls. The plurality of interior walls defines a recessed cavity. Optionally, one or more of the one or more of the one or more illumination sources, the infrared camera, the at least one first reflector, the at least one second reflector is/are disposed within the recessed cavity.

In some implementations, the one or more illumination sources may include a first column of illumination sources and a second column of illumination sources. A first reflector of the at least one first reflector is arranged about each illumination source forming the first column of illumination sources and the second column of illumination sources. The at least one second reflector includes a left second reflector and a right second reflector. The first column of illumination sources are arranged proximate the left second reflector. The second column of illumination sources are arranged proximate the right second reflector.

Optionally, the assembly may include a display connected to the computing resource and a user interface connected to the computing resource. One or more of the computing resource, the display and the user interface is/are disposed upon one of the plurality of exterior walls of the housing portion.

Optionally, the computing resource may be a tablet computer. The tablet computer also includes a display and a user interface. The tablet computer is disposed upon one of the plurality of exterior walls of the housing portion.

Optionally, the support structure includes a pod portion connected to the housing portion and an adjuster portion that connects the housing portion to the pod portion. The adjuster portion permits the housing portion to be pivoted, rotated and/or pitched relative to the pod portion.

Optionally, the support structure includes a leg portion connected to the housing portion and a linear guide bar connected to one or both of the leg portion and the housing portion. One or more of the leg portion and the linear guide bar includes one or more suction cups to permit one or more of the leg portion and the linear guide bar to be removably-attached to the surface of the test piece.

In some examples, the at least one first reflector is arranged relative to the surface of the test piece such that the light is not directed toward the surface of the test piece but rather parallel to the surface of the test piece.

Optionally, the system includes an electronic thermometer connected to the computing resource. The electronic thermometer measures ambient air temperature and the computing resource compares the comparing the ambient temperature to a detected temperature of the surface of the test piece.

Optionally, the motor may be coupled to the at least one second reflector by way of an axle in order to permit the at least one second reflector to be pivotally adjustable relative to a spatially fixed orientation of the one or more illumination sources and the at least one first reflector.

Optionally, the first spatial orientation of the at least one second reflector does not intersect with a path of the light and the second spatial orientation of the at least one second reflector intersects with a path of the light. Alternatively, the first spatial orientation of the at least one second reflector intersects with a path of the light and the second spatial orientation of the at least one second reflector intersects with a path of the light.

Optionally, the one or more illumination sources includes one or more flash lamps that creates a plasma for a few millisecond by an application of a high voltage across a pressurized gas tube. Alternatively, the one or more illumination sources includes one or more high intensity gas discharge lamps with large filaments. Alternatively, the one or more illumination sources includes one or more halogen lamps.

In some instances, the one or more illumination sources are point filaments that is/are approximately equal to or less than 0.25" that permit closer arrangement of the one or more illumination sources to the near focal point of the at least one first reflector so that the light is focused at the far focal point.

In some implementations, the at least one first reflector includes an internal reflection surface having an elliptical shape. Optionally, the internal reflection surface includes a polished finish to provide specular reflection. Optionally, the internal reflection surface includes an aluminum coating or a gold coating. The internal reflection surface is not a parabolic shape. The internal reflection surface is not a quasi-parabolic shape.

In some examples, the system does not include a spectral filter such that the light includes both visible light and infrared light.

Optionally, the at least one second reflector is substantially planar; alternatively, the at least one second reflector is slightly curved. Optionally, the at least one second reflector includes a specular reflection surface; alternatively, the at least one second reflector includes a slightly roughened reflection surface. The slightly roughened reflection surface may be brushed. The slightly roughened reflection surface may include patterned aluminum. The slightly roughened reflection surface (28) may include patterned gold.

Another aspect of the disclosure provides an assembly including an optically excited infrared nondestructive testing active thermography system. The optically excited infrared nondestructive testing active thermography system includes one or more illumination sources, at least one first reflector, at least one second reflector and a computing resource. The one or more illumination sources includes a first column of illumination sources and a second column of illumination sources. The at least one first reflector is arranged about each illumination source forming the first column of illumination sources and the second column of illumination sources. The at least one first reflector has a near focal point and a far focal point. The one or more illumination sources is/are positioned at least proximate the near focal point of the at least one first reflector. The at least one second reflector is positioned at least proximate the far focal point. The at least one second reflector includes a left second reflector and a right second reflector. The first column of illumination sources are arranged proximate the left second reflector. The second column of illumination sources are arranged proximate the right second reflector. The computing resource is communicatively-coupled to a motor that is coupled to the at least one second reflector for manipulating each of the left second reflector and the right second reflector between at least a first spatial orientation and a second spatial orientation. At least one of the first spatial orientation and the second spatial orientation results in each of the left second reflector and the right second reflector reflecting light that originates from the one or more illumination sources. The light is directed toward each of the left second reflector and the right second reflector as a result of the light being directly propagated from the one or more illumination sources and reflected by the at least one first reflector.

In some implementations, the system also includes an infrared camera communicatively-coupled to the computing resource. Positioning of each of the left second reflector and the right second reflector in the first spatial orientation results in the light being substantially directly and indirectly blocked by each of the left second reflector and the right second reflector such that the light is not incident upon or detected by the infrared camera while the light is reflected by each of the left second reflector and the right second reflector toward a surface of a test piece.

In some examples, the system also includes an infrared camera communicatively-coupled to the computing resource. Positioning of each of the left second reflector and the right second reflector in the second spatial orientation results in the infrared camera detecting heat from the surface of the test piece that was heated as a result of the light that was reflected by each of the left second reflector and the right second reflector toward the surface of the test piece while heat emanating from one or more of the one or more illumination sources and the at least one first reflector is blocked by each of the left second reflector and the right second reflector such that the heat emanating from one or more of the one or more illumination sources and the at least one first reflector is not incident upon or detected by the infrared camera.

In some instances the assembly also includes a support structure that is connected to and supports one or more of the one or more illumination sources, the infrared camera, the at least one first reflector, each of the left second reflector and the right second reflector, the computing resource and the motor. The support structure includes a housing portion that is connected to and supports: the one or more of the one or more illumination sources, the infrared camera, the at least one first reflector, each of the left second reflector and the right second reflector, the computing resource and the motor. The housing portion includes a plurality of interior walls and a plurality of exterior walls. The plurality of interior walls defines a recessed cavity. One or more of: the one or more of the one or more illumination sources, the infrared camera, the at least one first reflector, each of the left second reflector and the right second reflector is/are disposed within the recessed cavity.

Optionally, the assembly also includes a display connected to the computing resource and a user interface connected to the computing resource. One or more of the computing resource, the display and the user interface is/are disposed upon one of the plurality of exterior walls of the housing portion. The computing resource may be a tablet computer. The tablet computer may also include a display and a user interface. The tablet computer may be disposed upon one of the plurality of exterior walls of the housing portion. Optionally, the support structure may be a pod portion connected to the housing portion. Optionally, the support structure may further include an adjuster portion that connects the housing portion to the pod portion, which may permit the housing portion to be pivoted, rotated and/or pitched relative to the pod portion.

Optionally, the support structure may include a leg portion connected to the housing portion and a linear guide bar connected to one or both of the leg portion and the housing portion. One or more of the leg portion and the linear guide bar may include one or more suction cups to permit one or more of the leg portion and the linear guide bar to be removably-attached to the surface of the test piece.

In some implementations, the at least one first reflector may be arranged relative to the surface of the test piece such that the light is not directed toward the surface of the test piece but rather parallel to the surface of the test piece.

Optionally, the system may include an electronic thermometer connected to the computing resource. The electronic thermometer measures ambient air temperature. The computing resource compares the ambient temperature to a detected temperature of the surface of the test piece.

In some examples, the motor is coupled, respectively, to each of the left second reflector and the right second reflector by way of a left axle and a right axle in order to permit each of the left second reflector and the right second reflector to be pivotally adjustable relative to a spatially fixed orientation of the one or more illumination sources and the at least one first reflector.

Optionally, the first spatial orientation of each of the left second reflector and the right second reflector does not intersect with a path of the light. The second spatial orientation of the at least one second reflector intersects with a path of the light.

Optionally, the first spatial orientation of each of the left second reflector and the right second reflector intersects with a path of the light. The second spatial orientation of each of the left second reflector and the right second reflector intersects with a path of the light.

Optionally, the one or more illumination sources includes one or more flash lamps that creates a plasma for a few millisecond by an application of a high voltage across a pressurized gas tube. Alternatively, the one or more illumination sources includes one or more high intensity gas discharge lamps with large filaments. Alternatively, the one or more illumination sources includes one or more halogen lamps.

In some instances, the one or more illumination sources are point filaments that is/are approximately equal to or less than 0.25" that permit closer arrangement of the one or more illumination sources to the near focal point of the at least one first reflector so that the light is focused at the far focal point. In some implementations, the at least one first reflector includes an internal reflection surface having an elliptical shape.

Optionally, the internal reflection surface of the at least one first reflector includes a polished finish to provide specular reflection. Alternatively, the internal reflection surface includes an aluminum coating or a gold coating.

The at least one first reflector includes an internal reflection surface that is not a parabolic shape. The at least one first reflector includes an internal reflection surface that is not a quasi-parabolic shape. The system does not include a spectral filter such that the light includes both visible light and infrared light.

Optionally, each of the left second reflector and the right second reflector is substantially planar. Alternatively, each of the left second reflector and the right second reflector is slightly curved. Optionally, each of the left second reflector and the right second reflector includes a specular reflection surface. Optionally, each of the left second reflector and the right second reflector includes a slightly roughened reflection surface. Optionally, the slightly roughened reflection surface is brushed. Optionally, the slightly roughened reflection surface includes patterned aluminum. Optionally, the slightly roughened reflection surface includes patterned gold.

In yet another aspect of the disclosure provides a method for operating the system including the steps of: arranging one or more illumination sources and at least one first reflector in a spatially fixed orientation; directing light along a path that is substantially parallel to a surface of a test piece; spatially manipulating at least one second reflector in order to intersect the at least one second reflector with the path for reflecting the light toward the surface of the test piece while preventing a lens of an infrared camera from imaging the surface of the test piece; and heating the surface of the test piece with the light that is redirected by the spatially manipulated at least one second reflector.

In some implementations, the spatially manipulating step includes oscillating the at least one second reflector for dynamically changing the reflected direction of the light by the at least one second reflector as the light is being reflected by the at least one second reflector toward the surface of the test piece.

In some examples, after the heating step, the method further includes the steps of spatially manipulating the at least one second reflector for arranging the at least one second reflector in a position for preventing the infrared camera from being exposed to heat arising from one or both of the one or more illumination sources and the at least one first reflector; permitting the lens of the infrared camera to view the surface of the test piece for imaging the surface of the test piece; processing the imaged surface of the test piece including converting the image to electronic signals. The processing step includes applying an adjustment to electronic signals converted from images collected during an extended excitation of the one or more illumination sources by shifting a time assigned to the electronic signals so that at time t=0 indicates a midpoint of a heating period of the surface of the test piece.

In some instances, the method also includes the steps of: after the heating step, further spatially manipulating the at least one second reflector for arranging the at least one second reflector in a position for preventing the infrared camera from being exposed to heat arising from one or both of the one or more illumination sources and the at least one first reflector; permitting the lens of the infrared camera to view the surface of the test piece for imaging the surface of the test piece; processing the imaged surface of the test piece including converting the image to electronic signals. The processing step includes: applying an adjustment to electronic signals converted from images collected during an extended excitation of the one or more illumination sources by shifting a time assigned to the electronic signals so that at time t=0 indicates a midpoint of a heating period of the surface of the test piece; and correcting the temperature of the surface of the test piece using:

$$T_{corr}(t) = \frac{T_{raw}(t)}{2\sqrt{t} * \left(\sqrt{t + \frac{\tau}{2}} - \sqrt{t - \frac{\tau}{2}}\right)}$$

In some implementations, the method includes: after the heating step, further spatially manipulating the at least one second reflector for arranging the at least one second reflector in a position for preventing the infrared camera from being exposed to heat arising from one or both of the one or more illumination sources and the at least one first reflector; permitting the lens of the infrared camera to view the surface of the test piece for imaging the surface of the test piece; processing the imaged surface of the test piece including converting the image to electronic signals. The processing step includes: applying an adjustment to electronic signals converted from images collected during an extended excitation of the one or more illumination sources by shifting a time assigned to the electronic signals so that at time t=0 indicates a midpoint of a heating period of the surface of the test piece; and correcting the electronic signals for convection errors using:

$$T(t) = T_{det}e^{ht} - T_{amb}$$

In some examples, after the heating step, further spatially manipulating the at least one second reflector for arranging the at least one second reflector in a position for preventing the infrared camera from being exposed to heat arising from one or both of the one or more illumination sources and the at least one first reflector; permitting the lens of the infrared camera to view the surface of the test piece for imaging the surface of the test piece; processing the imaged surface of the test piece including converting the image to electronic signals. The processing steps includes: applying an adjustment to electronic signals converted from images collected during an extended excitation of the one or more illumination sources by shifting a time assigned to the electronic signals so that at time t=0 indicates a midpoint of a heating period of the surface of the test piece collecting the electronic signals for background/emissivity errors using:

$$T(t) = \frac{T_{det} - (1-e)T_{bkgd}}{s}$$

Optionally, the spatially manipulating step includes: firstly arranging the at least one second reflector in a first position that that does not intersect the path while also preventing the lens of the infrared camera from imaging the surface of the test piece and secondly arranging the at least one second reflector in a second position that that intersects with the path while still preventing the lens of the infrared camera from imaging the surface of the test piece.

Optionally, prior to the directing the light step, utilizing the infrared camera for acquiring images of the surface of the test piece prior to heating the surface of the test piece.

In some instances, the directing the light step occurs in response to: applying a voltage to the one or more illumination sources; and only upon determining that a current reaches a threshold level, raising the voltage and then conducting the spatially manipulating step. After a period of time, application of the voltage is ceased, and, after the heating step, further spatially manipulating the at least one second reflector for arranging the at least one second reflector in a position for preventing the infrared camera from being exposed to heat arising from one or both of the one or more illumination sources and the at least one first reflector. The method further includes permitting the lens of the infrared camera to view the surface of the test piece for imaging the surface ($T_S$) of the test piece (T). The method also includes the steps of processing the imaged surface of the test piece, and the processing step includes applying an adjustment during an extended excitation of the one or more illumination sources by shifting a time assigned to each collected frame produced by the infrared camera so that at time t=0 indicates a midpoint of a heating period of the surface of the test piece.

DETAILED DESCRIPTION

The Figures illustrate exemplary embodiments of a nondestructive testing active thermography system and method for utilizing the same. Based on the foregoing, it is to be generally understood that the nomenclature used herein is simply for convenience and the terms used herein to describe various aspects of the invention should be given the broadest meaning by one of ordinary skill in the art.

For purposes of this disclosure, the terms extended pulse, extended pulse event, extended pulse heating event, extended pulse response, step function, step heat signal, step heating event are all generally synonymous and relate to NDT systems in which the duration of an excitation heating event extends in time for at least one or more frames of a camera.

For purposes of this disclosure, the terms delta function, delta excitation, delta impulse function, short duration light source, flash excitation, flash pulse, flash pulse, flash optical excitation, instantaneous heating signal, delta heating signal are all generally synonymous and relate to NDT systems in which the duration of an excitation heating event extends in time for less than one frame of a camera.

An exemplary optically excited infrared (OEIR) nondestructive testing (NDT) active thermography system is shown generally at 10 in FIGS. 1A-1D. The OEIR-NDT active thermography system 10 does not necessarily contact a test piece, T, which may be positioned proximate the OEIR-NDT active thermography system 10. Functionally, the OEIR-NDT active thermography system 10 may be employed to detect subsurface structural features of a test piece such as structural reinforcement members, imperfections or the like. The test piece, T, may be an aircraft component or an entire section of an aircraft. The examination may be performed on the fully assembled and operational aircraft during maintenance, or on the component after it has been removed from the aircraft, and, the imperfections therein may include, for example, water trapped within or between layers of a composite sandwich structure defining the test piece, T. In some instances, the OEIR-NDT active thermography system 10 inspects a portion of the test piece defined by an area (e.g., on the order of 1 sq. ft.) of the test piece, T, in a relatively short period of time (inspection time may typically range from 2-3 seconds to 2-3 minutes, depending on a number of factors including the size of the surface area of the test piece to be scanned and the thickness and thermal diffusivity of the test piece.

The OEIR-NDT active thermography system 10 includes a plurality of components such as, for example: one or more illumination sources 12, an imaging device (e.g. infrared (IR) camera) 14, a computing resource 16, at least one first reflector 18, at least one second reflector 20, a display 22 and a user interface 24. The computing resource 16 may be, for example, a digital computer, and may include, but is not limited to: one or more electronic digital processors or central processing units (CPUs) in communication with one or more storage resources (e.g., memory, flash memory, dynamic random access memory (DRAM), phase change memory (PCM), and/or disk drives having spindles)). The computing resource 16 may be communicatively coupled to each of the one or more illumination sources 12, the infrared (IR) camera 14, a motor 30 connected to the at least one second reflector 20, the display 22 and the user interface 24. The at least one first reflector 18 may be fixedly-disposed about the one or more illumination sources 12. In some instances, the computing resource 16, the display 22 and the user interface 24 may be integrated into a single device such as, for example, a tablet computer (see, e.g., reference numeral 44 in FIGS. 5A-5B).

The one or more illumination sources 12 emits one or more beams or rays of light, L. An exemplary embodiment shown in FIGS. 1A-1D includes one illumination source 12 whereas another exemplary embodiment shown in FIGS. 5A-8B includes six illumination sources 12.

The infrared (IR) camera 14 detects the intensity of the IR radiation emitted from the sample surface and converts the detected IR radiation into one or more electronic signals that are encoded with the information relating to the intensity of the detected IR radiation. The information can be assembled and used in numerous ways including converted to a series of time based images (viewable by a user on the display device 22) indicative of temperature change of a surface, $T_S$, of the test piece, T, that is heated as a result of light, L, impinging upon the surface, $T_S$. The camera 14 may convert the one or more images into one or more electronic output signals (such as digitally encoded data output signals). The computing resource 16 may, among other functions, provide means for analyzing the output of the IR camera 14 and means for adjusting a spatial orientation (e.g., an angle, $\theta_{OPEN}$ (see, e.g., FIG. 1B), $\theta_{CLOSED}$ (see, e.g., FIG. 1C), $\theta_A$ (see, e.g., FIG. 1D)) of the at least one second reflector 20 in order to direct the output of the one or more illumination sources 12 toward the surface, $T_S$, of the test piece, T.

Figure 1B:
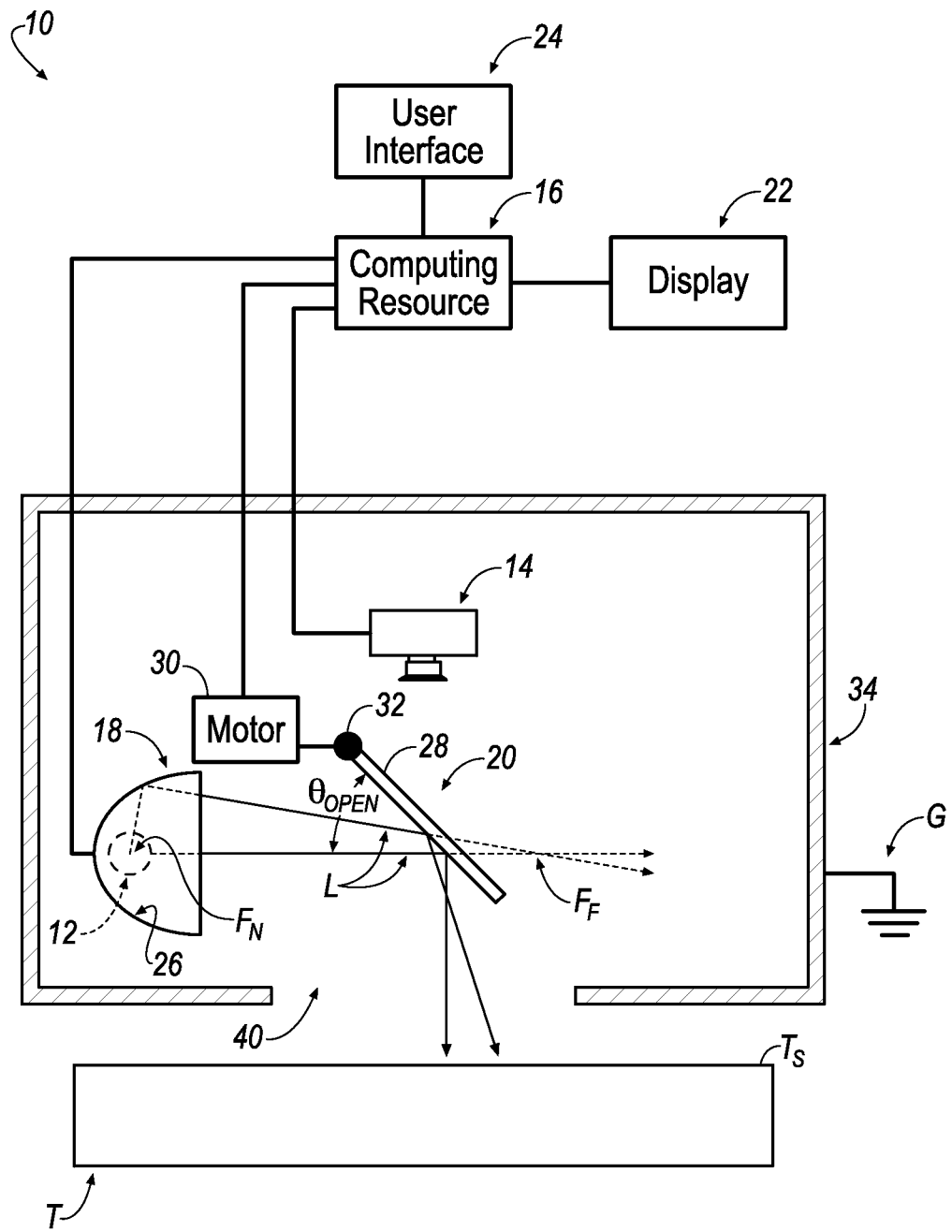
FIG. 1B is another view of the OEIR-NDT active thermography system of FIG. 1A.
Figure 1C:
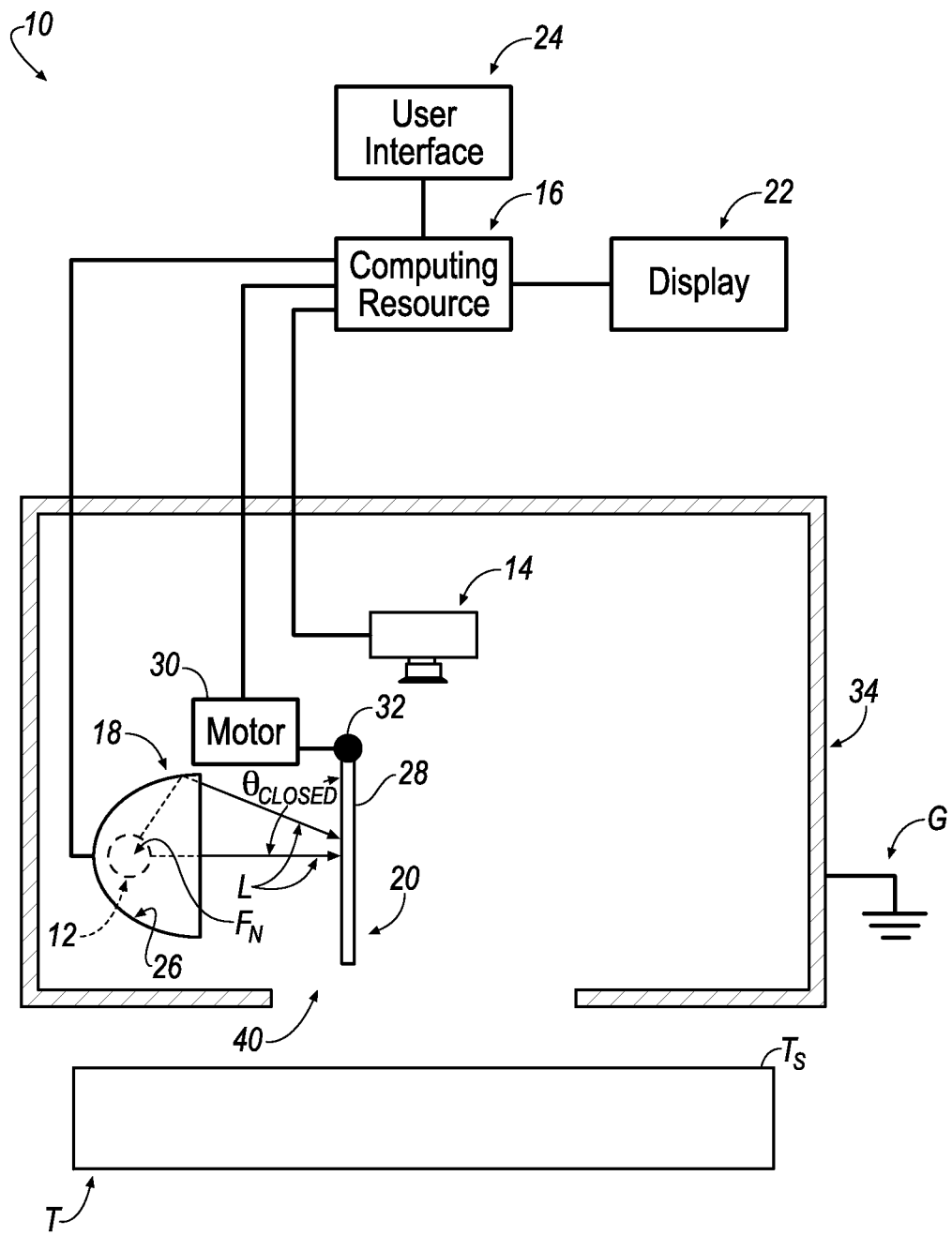
FIG. 1C is another view of the OEIR-NDT active thermography system of FIG. 1A.
Figure 1D:
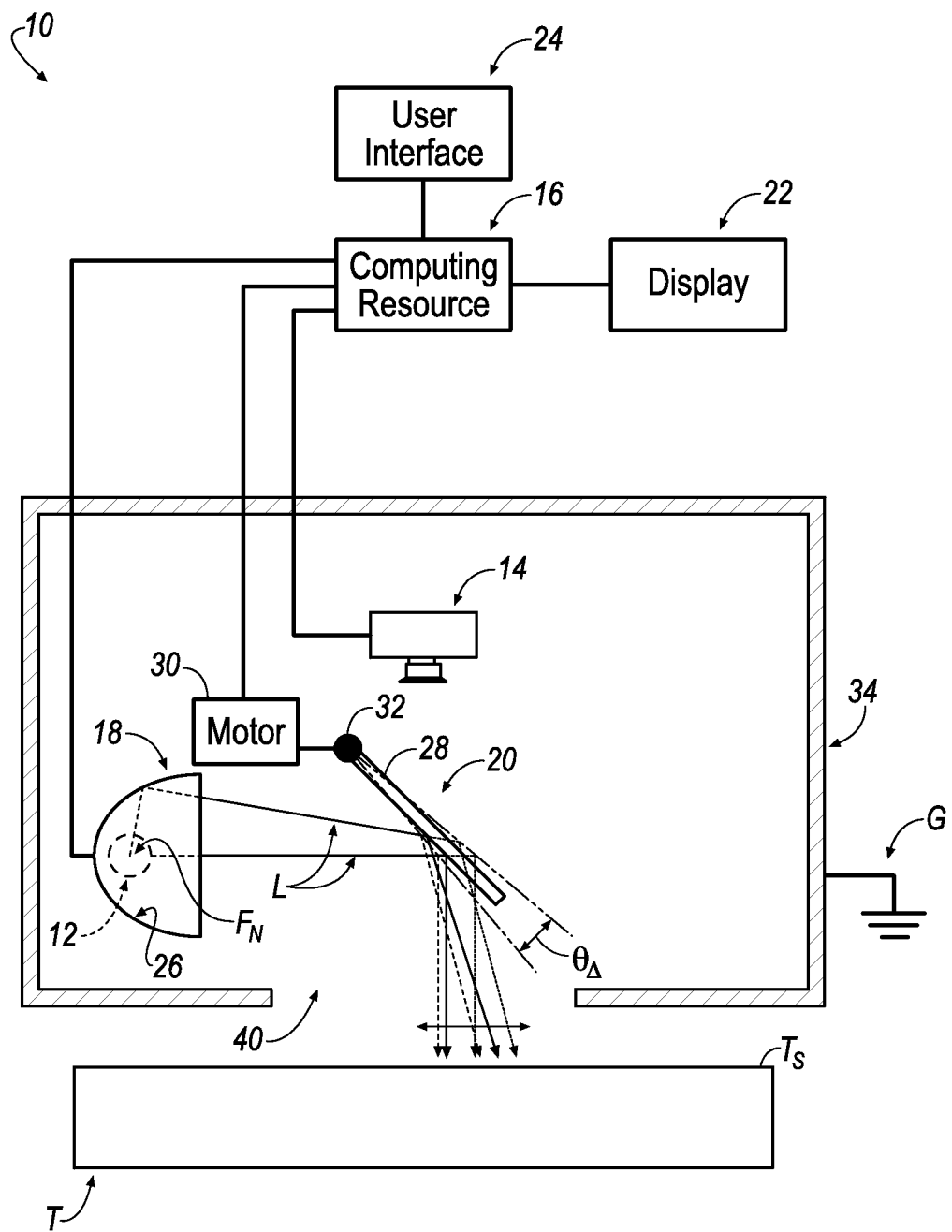
FIG. 1D is another view of the OEIR-NDT active thermography system of FIG. 1A.

In some instances, as seen in, for example, FIG. 1D, the at least one second reflector 20 may actively reflect the one or more beams or rays of light, L, impinging upon the surface, $T_S$, of the test piece, T. The term "active" in the context of "actively reflecting" may mean that computing resource 16 is capable of selectively adjusting a spatial orientation of the at least one second reflector 20 when the one or more illumination sources 12 is/are activated in order to dynamically change (e.g. sweep back and forth continuously) the path of the one or more beams or rays of light, L, emitted by the one or more illumination sources 12. In some instances, once the at least one second reflector 20 is spatially adjusted, the at least one second reflector 20 may remain in a selectively-fixed orientation (as seen in, e.g., FIG. 1B or 1C). When actively-adjusted by computing resource 16 and motor 30 (as seen in, e.g., FIG. 1D), the at least one second reflector 20 may, for example, oscillate back and forth in a sweeping motion thereby sweeping the light L across an area of $T_S$. The display 22 may display a visual depiction of the infrared radiation captured by IR camera 14. The user interface 24 may permit a user to activate, deactivate or control any component 12-16, 20-24 of the OEIR-NDT active thermography system 10.

In some instances, the one or more illumination sources 12 may include one or more short duration light sources, such as, for example, one or more flash lamps, where a plasma is created for a few millisecond by the application of a high voltage across electrodes in a pressurized gas tube. The combination of flash optical excitation and high speed IR imaging may be employed to perform precise quantitative measurements, particularly in metals or high thermal diffusivity materials, such as, for example, measurement of wall thickness in aircraft turbine blades, T, or measurement of porosity in ceramic matrix composite materials, T. In other instances, the one or more illumination sources 12 may include one or more continuous high intensity lamps utilizing an arc across energized electrodes, or a current heated filament in a pressurized gas tube, e.g. a tungsten filament in a halogen filled quartz or glass tube. Although the instantaneous flux of continuous sources is low compared to flash sources, the total amount of energy delivered to the sample can be significantly higher than that delivered by a flash source because the duration of the illumination increases. For thick or low thermal diffusivity materials, such as carbon or glass fiber reinforced polymer composites, continuous sources, applied for periods ranging from a few seconds to several minutes, provide a relatively inexpensive means of excitation.

Inclusion of the at least one second reflector 20 in the OEIR-NDT active thermography system 10 for actively reflecting the light output, L, of the one or more illumination sources 12 permits the OEIR-NDT active thermography system 10 to address different levels of performance, cost and complexity not provided by other conventional imaging systems, while coping with many challenges that limit performance and present obstacles to implementation in relation to conventional imaging systems. Exemplary issues addressed by the OEIR-NDT active thermography system 10 include: (1) uniformity issues, (2) reflection artifact issues, (3) poor temporal definition of the excitation pulse issues, and (4) convection issues.

Regarding (1) uniformity issues, the methodology associated with the OEIR-NDT active thermography system 10 assumes that the light excitation, L, is distributed in a reasonably uniform manner over a test area such as at least a portion of the surface, $T_S$, of the test piece, T. Absolute uniformity of light distribution across a test piece surface $T_S$ is rarely required but, for thicker test pieces, T (such as, e.g., wind turbine blades where acquisition times may be on the order of several minutes or longer), the effect of lateral thermal gradients may be significant enough to mask a desired signal associated with heat propagating into the test piece, T. Satisfactory uniformity may be achieved even when one or more "real" (i.e. non-idealized) illumination sources 12 are used, such as, for example, one or more high intensity lamps with large filaments. As the filament (or arc, in a gas discharge lamp) becomes larger, collimation or focusing becomes weaker and satisfactory uniformity becomes more difficult to achieve. In order to compensate, more or larger optics are employed, thereby otherwise adding to the size, weight and cost of the system).

Regarding (2) reflection artifact issues, the OEIR-NDT active thermography system 10 mitigates post-excitation radiation that would otherwise be introduced by the one or more illumination sources 12. During normal operation, structure associated with one or more of the illumination sources 12 (such as a reflector or mounting fixtures) or the lamp itself may become heated by the generated light, causing an increase in emitted IR radiation to occur, and continue after the intended excitation has terminated. This radiation may impinge directly on the IR camera lens, or on the test piece surface, where it may be reflected back into the IR camera, depending on the emissivity of the test piece surface. In either case, the stray radiation may act to modify or obscure the emitted IR radiation signal that is used to evaluate the test piece.

Regarding (3) poor temporal definition of the excitation pulse, the OEIR-NDT active thermography system 10 overcomes issues typically associated with the use of multiple illumination sources 12 to generate a step function process for heating the test piece, T. In some instances, when the one or more illumination sources 12 are halogen lamps are electrically driven by a step excitation voltage, the one or more illumination sources 12 are simply turned on and off to create a step heating function, which is convenient for many signal processing methods. However, the optical output of the one or more halogen lamps 12 does not closely track the rise and fall times of the step excitation voltage applied to it, because both onset of the output illumination event and the decay of the output illumination are not instantaneous. As a result, what is presumed to be a "clean" step illumination function having vertical, or nearly vertical, rise and fall periods, may, in reality, resemble a triangle wave. This result is not only inefficient, but it also may dilute the effect of some signal processing or measurement methods.

Regarding (4) convection, the OEIR-NDT active thermography system 10 overcomes issues that occur as a consequence of the fact that the test piece is intentionally heated to a temperature greater than that of the fluid (air) surrounding it, so that convective cooling of the test piece surface occurs in addition to the intended cooling due to conduction from the surface into the sample bulk. In many instances, convection cooling effects are negligible compared to heat conduction, particularly when data acquisition times are relatively short (less than or equal to approximately 5 seconds). However, for thick or low-thermal diffusivity test pieces, more heat of the sample surface may be required in order to keep the emitted IR radiation signal level detected by the IR camera above the electronic and background noise level over the duration of a longer data acquisition sequence. In such cases, true indications (i.e. sub-surface information) may be masked, or false indications due to convective cooling may be made evident.

Unlike some systems that may utilize "large", high power lamps (e.g., often with a filament that is several inches long in to cover a large area (e.g., >500 W halogen lamps with 6" filaments or flashlamps with 6400 Joule output)), the one or more illumination sources 12 of the OEIR-NDT active thermography system 10 achieves much better control of the light, L, using reflective or transmissive optics when one or more "smaller" illumination sources 12 (filament or arc) is/are used. As lamp output increases (in association with "large" high power lamps), so does the size of its filament or arc, and the optical behavior of the lamp becomes more complex, compared to a point source. Therefore, in some instances, the one or more illumination sources 12 of the OEIR-NDT active thermography system 10 utilizes "small" sources (e.g. filaments <0.25") that can be placed more precisely at a near focal point, $F_N$, of the at least one first reflector 18, so that the emitted light, L, can be directed more accurately and greater efficiency can be achieved. Although these "small" sources generate less energy than "larger" sources, a plurality of the small sources may be utilized to fill an entire target area of a test piece, T, and, since the small sources can be more accurately focused, more of the emitted light, L, falls on the target of the test piece, T. The use of "small" sources also allows control over the distribution of light, L, at the output plane more effectively.

The "small" one or more illumination sources 12 may also be characterized as (and modeled as) "point" sources. Each small one or more point illumination sources 12 are arranged at the near focal point, $F_N$, of the at least one first reflector 18 so that the beam of light, L, is focused at a far focal point, $F_F$. An internal reflection surface 26 of the at least one first reflector 18 includes an ellipsoidal shape, which may also have a polished finish to enable specular reflection. In some instances, the internal reflection surface 26 may be coated with aluminum, gold, or other material that will efficiently reflect both visible light, L, and IR light, L, that is output from the one or more illumination sources 12. Further, the at least one first reflector 18 may be oriented in a manner such that the light, L, irradiated from the one or more illumination sources 12 is not directed toward (i.e., not substantially perpendicularly toward) the surface, $T_S$, of the test piece, T, but, rather, parallel to the surface, $T_S$, of the test piece, T, or substantially parallel to the surface, $T_S$, of the test piece, T.

As described above, the OEIR-NDT active thermography system 10 uses the entire spectral output (i.e., both of the visible light, L, and IR light, L) of the one or more illumination sources 12. Some conventional imaging systems may only utilize the visible output of the one or more illumination sources 12 to heat a test piece by employing spectral filters to block the IR energy that is emitted by the one or more illumination sources 12. This is a very inefficient strategy, since only approximately 10% of the output of a halogen lamp at 3200 K is in the visible spectrum. Furthermore, the blocked IR energy heats the side of the filter nearest the lamp, and that energy is conducted through the filter to the opposite side, where it is emitted as IR radiation that may be reflected off of the sample surface into the IR camera. In an embodiment, the OEIR-NDT active thermography system 10 does not employ spectral filters between the illumination source and the test piece T. This approach allows the entire spectrum of energy emitted by the one or more illumination sources 12 to reach the surface, $T_S$, of the test piece, T by eliminating the use of spectral filters. However, the OEIR-NDT active thermography system 10 prevents reflection artifacts by moving the at least one second reflector 20 into the path (as seen in FIG. 1C) of the one or more beams or rays of light, L, to block the one or more illumination sources 12 after the illumination event has ceased, so that the warm one or more illumination sources 12 and fixtures associated therewith do not project past illumination event radiation onto the surface, $T_S$, of the test piece, T.

In an embodiment, the at least one first reflector 18 is not a parabolic or a quasi-parabolic reflector (i.e., as stated above, the first reflector is an elliptical reflector); parabolic or quasi-parabolic reflectors are designed to minimize beam divergence and are typically utilized for work lights or photography, and, as such, do not to provide high collimation or uniform output at a near field target. Because the at least one first reflector 18, however, is an elliptical reflector, the output focal distance is small, relative to the lamp to target distance. Rays of light, L, from the one or more illumination sources 12 exit the at least one first reflector 18 and pass through the output focal point, $F_F$, and then diverge until they strike the target (i.e. the beam striking the target is defocused, relative to the target); this is a much more efficient scheme when compared to parabolic or quasi-parabolic reflectors, as the at least one first reflector 18 directs all light, L, emanating from the at least one first reflector 18 to strike the target without the use of a reflecting hood to confine stray, diverging beams. The at least one first reflector 18 also facilitates a more compact design for the OEIR-NDT active thermography system 10, since the at least one first reflector 18 is small, compared to parabolic or quasi-parabolic reflectors designed to illuminate an equivalent area. Parabolic reflectors are designed to collimate a point source, but they are less effective for an extended (non-point) source. You could accomplish the function of an elliptical reflector with a parabolic reflector in combination with a lens. In this application 10, elliptical reflectors are the most efficient approach (both cost and packaging).

The at least one second reflector 20 may be substantially planar or near slightly curved. A finished reflection surface 28 of the at least one second reflector 20 may be specular. In other examples, the finished reflection surface 28 may be slightly roughened (e.g. the finished reflection surface 28 may be brushed or provided with patterned aluminum or a gold) to diffuse the one or more beams or rays of light, L, slightly, so that the image of the filament or other distinct features of the one or more illumination sources 12 are scattered over the target area of the surface, $T_S$, of the test piece, T, and, are therefore, not imaged onto the target area of the surface, $T_S$, of the test piece, T.

In some instances, the configuration of the at least one second reflector 20 in the OEIR-NDT active thermography system 10 may be ideal for near field use, as the OEIR-NDT active thermography system 10 can be implemented in a compact unit. However, by replacing the at least one second reflector 20 with an off-axis paraboloid, the OEIR-NDT active thermography system 10 can project a slowly diverging beam, L, into the far field; the same corrections can be applied to yield a step-heating signal that is identical to an instantaneously heated one (i.e. delta heating signal).

In some instances, the exemplary embodiment of FIGS. 1A-1D includes one second reflector 20 whereas the exemplary embodiment of FIGS. 5A-8B includes two second reflectors 20 including a left second reflector 20a and a right second reflector 20b. As seen in FIG. 1A, the at least one second reflector 20 may be spatially arranged in a manner that does not intersect with a path of the one or more beams or rays of light, L. However, as seen in FIGS. 1B-1D, the at least one second reflector 20 may be spatially manipulated (as a result of a signal being sent from the computing resource 16 to a small motor (e.g. a stepper or servomotor) 30 connected to an axle 32 that is the axle could be connected to a portion of a second reflector, such as, for example, an edge of the at least one second reflector 20 in order to cause the at least one second reflector 20 to intersect with a path of the one or more beams or rays of light, L. As seen in FIG. 1B, once the at least one second reflector 20 is spatially manipulated (as a result of a signal being sent from the computing resource 16 to the small motor 30), the at least one second reflector 20 may be arranged between the far focal point, $F_F$; and reflector 18. Although the at least one second reflector 20 is shown arranged between the far focal point, $F_F$, and reflector 18. the at least one second reflector 20 may be alternatively selectively arranged to be aligned with and intersect the far focal point, $F_F$. Alternatively, once the at least one second reflector 20 is spatially manipulated as a result of a signal being sent from the computing resource 16 to the small motor 30, the at least one second reflector 20 may be selectively arranged beyond the far focal point, $F_F$.

As seen in FIG. 1B, once the at least one second reflector 20 is spatially manipulated to an "open position" in order to intersect with a path of the one or more beams or rays of light, L, the at least one second reflector 20 may be arranged at an angle, $\theta_{OPEN}$ (e.g. approximately) 45°. The angle, $\theta_{OPEN}$, is referenced from an optical axis of the one or more illumination sources 12 that emits one or more beams or rays of light, L, that is substantially parallel to the surface, $T_S$, of the test piece, T. When arranged at the "open position" angle, $\theta_{OPEN}$, the at least one second reflector 20 reflects the one or more beams or rays of light, L, over substantially all of a target area of the surface, $T_S$, of the test piece, T.

As seen in FIG. 1C, in another example, once the at least one second reflector 20 is spatially manipulated to a "closed position" in order to intersect with a path of the one or more beams or rays of light, L, the at least one second reflector 20 may be arranged at an angle, $\theta_{CLOSED}$ (e.g. approximately 90°). The angle, $\theta_{CLOSED}$, is referenced from an optical axis of the one or more illumination sources 12 that emits one or more beams or rays of light, L, that is substantially parallel to the surface, $T_S$, of the test piece, T. When arranged at the "closed position" angle, $\theta_{CLOSED}$, the at least one second reflector 20 may "block" or reflect the one or more beams or rays of light, L, back toward the at least one first reflector 18 such that none of the one or more beams or rays of light, L, are directed toward the target area of the surface, $T_S$, of the test piece, T (i.e., no energy associated with the one or more beams or rays of light, L, reaches the surface, $T_S$, of the test piece, T; this eliminates the possibility of reflection artifacts. Toward this end, the at least one second reflector 20 may be constructed with a double wall (e.g., a pair of walls with an insulator disposed there between such as, for example, air), so that the once the at least one second reflector 20 is warmed, the at least one second reflector 20 does not radiate heat toward the surface, $T_S$, of the test piece, T. Additionally, when the at least one second reflector 20 is arranged in the "closed position", the IR camera 14 is permitted to have an unobstructed sightline to the sample surface while also being shielded from the one or more illumination sources 12.

As seen in FIG. 1D, in another example, once the at least one second reflector 20 is spatially manipulated in order to intersect with a path of the one or more beams or rays of light, L, the at least one second reflector 20 may be actively manipulated (i.e. swept) between a range of angles, $\theta_A$ (e.g. between approximately 0° as seen in FIG. 1A and 90° as seen in FIG. 1C). When arranged between the range of angles, $\theta_A$, the at least one second reflector 20 may, for example, be spatially adjusted in an oscillating manner, in order to actively reflect the one or more beams or rays of light, L, at all or selected portions of a target area of the surface, $T_S$, of the test piece, T.

Unlike the exemplary embodiment of the OEIR-NDT active thermography system 10 described at FIG. 1B, the oscillating movement of the at least one second reflector 20 of the exemplary embodiment of the OEIR-NDT active thermography system 10 described at FIG. 1D permits the one or more beams or rays of light, L, to be spread during the heating of the surface, $T_S$, of the test piece, T. Such movement of the at least one second reflector 20 permits the one or more beams or rays of light, L, to "paint" or scan (as seen in, e.g., FIGS. 8A-8B) over a region of the surface, $T_S$, of the test piece, T, by way of the oscillating motion of the at least one second reflector 20. The oscillating movement of the at least one second reflector 20 allows the OEIR-NDT active thermography system 10 to control the overlap between adjacent beams of the one or more beams or rays of light, L, to avoid generation of hot or cold spots on the surface, $T_S$, of the test piece, T, and, as a result, uniformity may be improved upon. The oscillating movement of the at least one second reflector 20 also blurs features of the filament or arc of the one or more illumination sources 12 that may be imaged onto the surface, $T_S$, of the test piece, T. Since the focus of the one or more beams or rays of light, L, is slightly before or after the open position of the at least one second reflector 20, a small oscillating motion of the at least one second reflector 20 can result in significant motion in the far field. This oscillation can take place over one, or more oscillation cycles to ensure that the test sample has reached the desired temperature.

As seen above in FIGS. 1B and 1D, in addition to the at least one second reflector 20 reflecting the one or more beams or rays of light, L, toward the surface, $T_S$, of the test piece, T, the at least one second reflector 20 also provides a second function by being arranged in front of a line of sight of a lens of the IR camera 14 for the purpose of "blocking" or shielding the lens of the IR camera 14 when the surface, $T_S$, of the test piece, T, is being heated by the one or more beams or rays of light, L, reflected by the finished reflection surface 28 of the at least one second reflector 20. The arrangement of the at least one second reflector 20 as described above protects the lens and other structure of the IR camera 14 from being heated during the above-described excitation period. If the at least one second reflector 20 did not block or shield the IR camera 14 as described above, the lens or detector of an IR camera 14 may be heated and internal electronic noise in the IR camera 14 may increase, thereby resulting in a spatial pattern being superimposed on the image of the object field. While this effect may be negligible, in some circumstances it can be significant if IR energy from the one or more illumination sources 12 passes into the lens and detector, either directly, as stray light, or indirectly, by reflection off the surface, $T_S$, of the test piece, T. Such direct heating to the IR camera 14 may cause the detector to become saturated, nonlinear, uncalibrated or noisy, and, even further, the lens of the IR camera 14 may remain heated and act as a secondary heat source in the field of view of the camera. Even heating of the body of the IR camera 14 may also cause other undesirable effects. The OEIR-NDT active thermography system 10 eliminates this possibility by exploiting the spatial manipulation of the at least one second reflector 20 for the purpose of blocking the IR camera 14 during the heating period so that the lens and overall body of the IR camera 14 does not view or is otherwise exposed to the surface, $T_S$, of the test piece, T, until heating of the surface, $T_S$, of the test piece, T, is complete.

Although the OEIR-NDT active thermography system 10 eliminates usual sources of noise and artifacts, including post-excitation reflection artifacts, other undesirable artifacts may occur as a result of stray IR radiation from personnel or equipment moving through the inspection area during data acquisition. Such sources can be eliminated with the use of a simple shroud or skirt (not shown) that surrounds the area between the OEIR-NDT active thermography system 10 and the test piece, T. The shroud or skirt may be, for example, a tent (not shown) attached to the OEIR-NDT active thermography system 10. The shroud or skirt performs no optical function other than to isolate the OEIR-NDT active thermography system 10 from unwanted radiation (existing systems sometimes use a hood as part of the optical system to direct light onto the target), so it may be constructed from a fabric or flexible material that blocks light, although complete extinction is not essential (aluminized Mylar, for example, would be sufficient). The shroud or skirt may have a section that can be opened after an area has been inspected, using snaps, zippers, VELCRO® or other means, so that results of the inspection computed by the OEIR-NDT active thermography system 10 can be transferred to the actual sample as described in U.S. Pat. No. 6,795,784, the totality of which is hereby incorporated by reference.

The computing resource 16 may send a signal to the one or more illumination sources 12 in order to apply a voltage to the one or more illumination sources 12. When voltage is applied to the one or more illumination sources 12, a period of time (e.g. such as 0.5 seconds may pass until the filament has become fully heated such that the one or more illumination sources 12 may reach its full output state. In order to extend the life of the one or more illumination sources 12, it is advantageous to gradually bring the one or more illumination sources 12 to its maximum output state as to initially limit the in-rush of current flow. One method of accomplishing this is to enable the computing resource 16 to interfere with a reactance circuit (not shown) to initiate and limit the flow of current through the filament of the one or more illumination sources 12, and remove the reactance when a designated current threshold is reached or when a prescribed period of time has lapsed. Other current control schemes could be used such as having computing resource 16 interface with a first current source $I_1$ apply a current through sources 12 for a first predetermined duration of time $T_1$, and thereafter a second current source, $I_2$, could be used to add to (i.e. supplement) the current supplied by $I_1$. This initiation process may occur when second reflector 20 is arranged in the "closed position" as seen in FIG. 1C. The at least one second reflector 20 may then be spatially manipulated to the "open position" as seen in FIG. 1B or 1D after the filament of the one or more illumination sources 12 reaches its maximum output state. Similarly, at the end of the heating period, the at least one second reflector 20 may be spatially manipulated back to the "closed position" as seen in FIG. 1C before the filament of the one or more illumination sources 12 is turned off.

The net effect described above may result in excitation that closely approximates a true (i.e. ideal) step heating function, which is desirable for both efficiency and subsequent signal processing operations. The OEIR-NDT active thermography system 10 does not begin excitation until the one or more illumination sources 12 reach their maximum radiation output state, and, the OEIR-NDT active thermography system 10 does not shut the one or more illumination sources 12 off until the one or more illumination sources 12 are blocked by the at least one second reflector 20 (as seen in FIG. 1C). As a result, the output is a true (or very close to a true) rectangular step function, which is a much more efficient excitation scheme arrangement than conventional systems where the step is achieved by simply using the voltage step signal that drives the illumination source as the means of creating the step illumination pattern on the test piece surface $T_S$. The OEIR-NDT active thermography system 10 also facilitates the use of post processing signal processing techniques because approaches that assume a step function can be more accurately employed.

When the OEIR-NDT active thermography system 10 includes more than one illumination sources 12, the more than one illumination sources 12 may illuminate all of a target area of the surface, $T_S$, of the test piece, T, thereby covering the entire field of view of the IR camera 14. In some instances, the more than one illumination sources 12 are arranged symmetrically with respect to the lens of the IR camera 14. In other examples, the more than one illumination sources 12 are arranged asymmetrically with respect to the lens of the IR camera 14. In instances where the OEIR-NDT active thermography system 10 includes more than one illumination sources 12 (as seen in, for example, an exemplary embodiment of FIGS. 5A-8B), each illumination source 12 may have its own first reflector 18.

Regarding data acquisition and signal processing, the computing resource 16 of the OEIR-NDT active thermography system 10 may be used for qualitative analysis, even though the timing of the excitation of the one or more illumination sources 12 is less precise than flashlamp-based systems (in flashlamp based systems the duration of the excitation pulse is typically less than one camera frame and more specifically is on the order of a few milliseconds or less). This contrast between system 10 and more precise flashlamp based systems is particularly stark for portable systems, where inexpensive uncooled IR microbolometers cameras, which are noisier and slower than laboratory models, are attractive, and sensitivity and speed may be sacrificed to reduce the size and cost of the system. The OEIR-NDT active thermography system 10 may optimize the quality of generated data so that results comparable to larger and more expensive laboratory units can be achieved. In an example, the IR camera 14 may acquire a sequence of images before heating of the surface, $T_S$, of the test piece, T, is initiated; preheating data provided from the IR camera 14 to the computing resource 16 will serve as a baseline, so that the temperature response to the applied heating of the surface, $T_S$, of the test piece, T, can be measured. In some instances, the sightline of the IR camera 14 may blocked by the at least one second reflector 20 as described above in FIG. 1B or 1D during the heating period, and, then a sequence of data may be acquired by the computing resource 16 from the IR camera 14. The length of the sequence of data may depend on the thermal properties and geometry of the test piece, T. The completed sequence is processed using the one, or more Thermographic Signal Reconstruction (TSR) methods, that are disclosed in U.S. Pat. Nos. 7,699,521; 8,449,176; 6,585,146; 6,795,784; 6,065,072; 7,554,086; 7,083,327; 5,683,181; 7,186,981; 5,631,465; 6,516,084; 6,751,342; 7,724,925; and 8,287,183 and U.S. Ser. Nos. 61/881,278; 13/648,806 and Ser. No. 13/653,168 all of which are hereby incorporated by reference.

Figure 2:
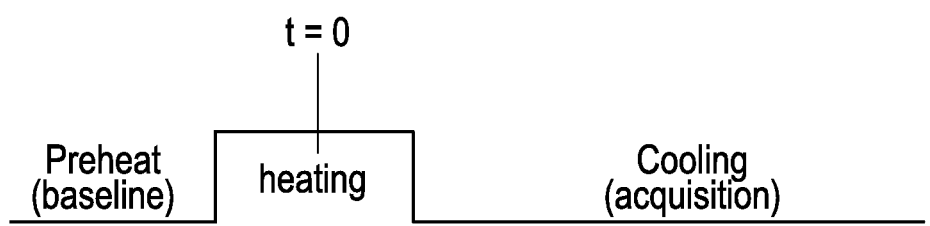
FIG. 2 is an exemplary timing diagram illustrating an time shift adjustment assigned to each collected frame produced by a camera of the OEIR-NDT active thermography system of FIGS. 1A-1D.
Figure 3B:
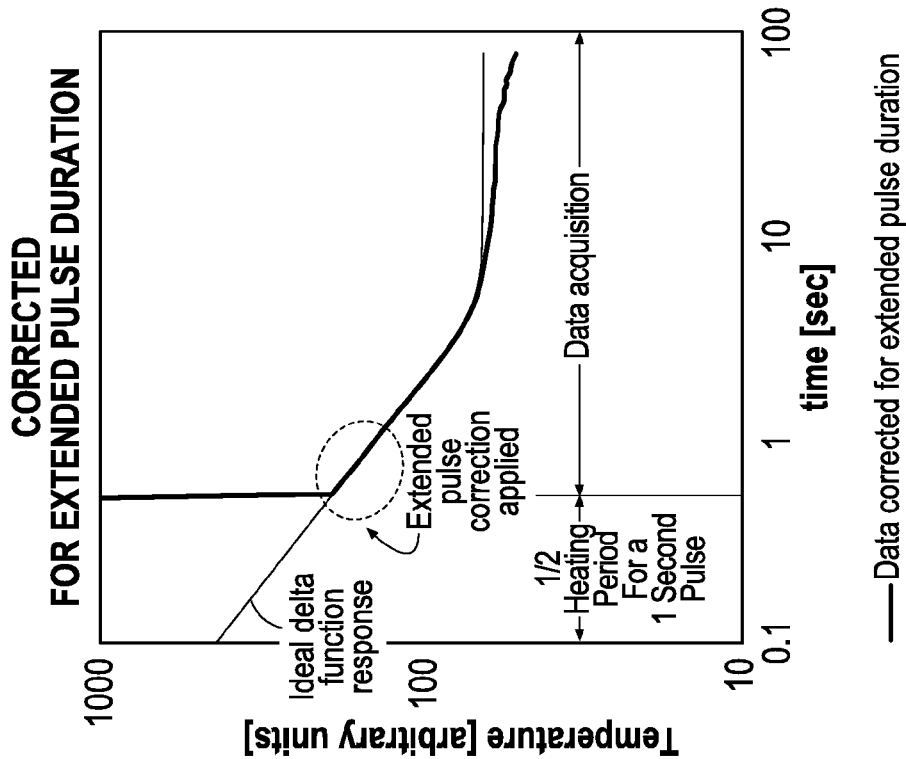
FIG. 3B is an exemplary timing diagram of the thermal response of a portion of a surface, $T_S$, of a test piece, T, to a one second excitation pulse, wherein the thermal response is not corrected for errors that result from the duration of the one second excitation pulse.
Figure 3A:
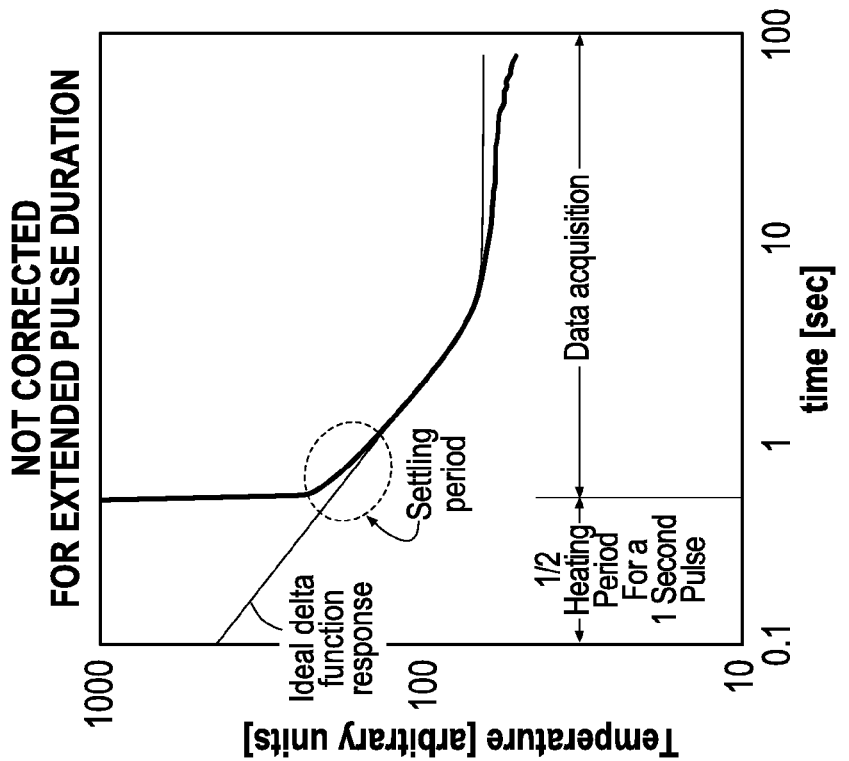
FIG. 3A is an exemplary timing diagram of the thermal response of a portion of a surface, $T_S$, of a test piece, T, to a one second excitation pulse, wherein the thermal response is not corrected for errors that result from the duration of the one second excitation pulse.
Figure 4B:
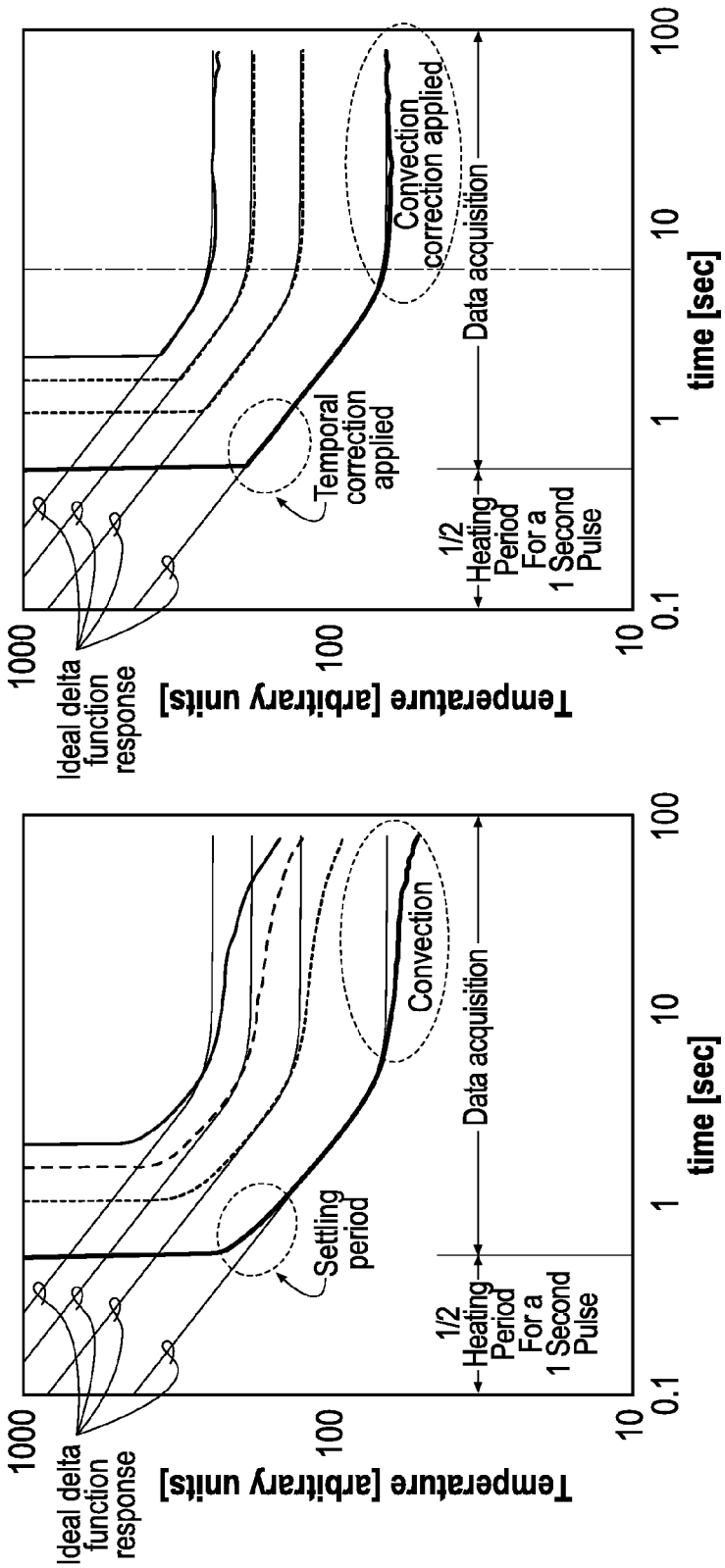
FIG. 4B is an exemplary timing diagram of the thermal response of a portion of a surface, $T_S$, of a test piece, T, to a one second, two second, three second, and four second excitation pulse, wherein the thermal response is corrected for errors that result from the duration of the excitation pulses or the errors that result from convection.
Figure 4A:
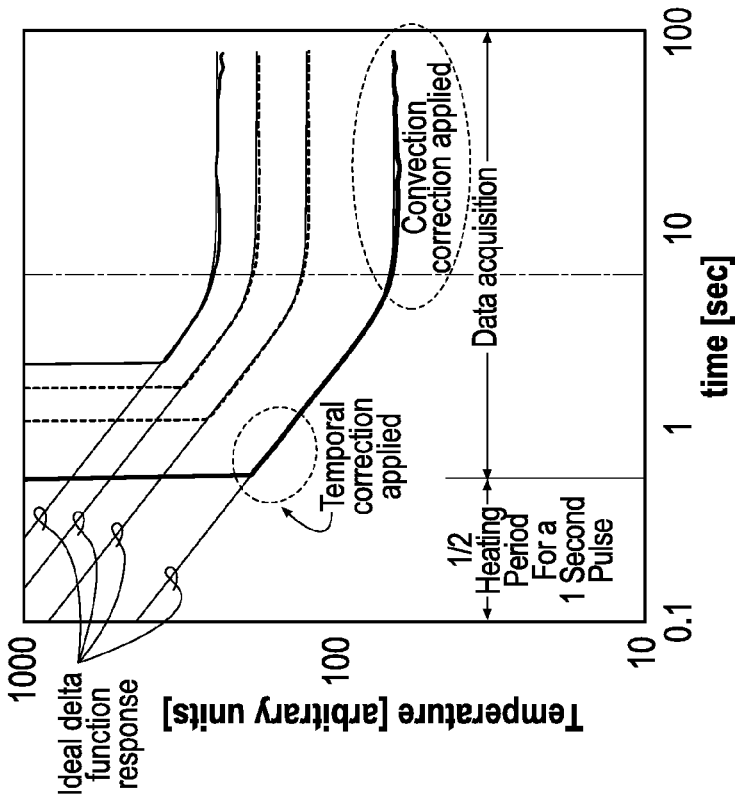
FIG. 4A is an exemplary timing diagram of the thermal response of a portion of a surface, $T_S$, of a test piece, T, to a one second, two second, three second, and four second excitation pulse, wherein the thermal response is not corrected for errors that result from the duration of the excitation pulses or the errors that result from convection.

Although the TSR method can be applied to the acquired data by using the steps described in the references which are incorporated by reference herein, it may be desirable to make some further adjustments when an extended excitation (i.e. step function), rather than instantaneous excitation (i.e. delta function) of the one or more illumination sources 12 is used. Referring to FIG. 2, one such adjustment is to shift the time assigned to each collected frame produced by the IR camera 14 so that time t=0 indicates the midpoint of the heating period of the surface, $T_S$, of the test piece, T.

The TSR method may be attractive because of the simplicity of interpretation it provides, based on the logarithmic derivatives of the surface temperature time history. For instantaneous, uniform excitation of the one or more illumination sources 12, the temperature vs. time plot of the temperature of the surface, $T_S$, for an infinitely thick, homogeneous sample, T, is a straight line, and its $1^{st}$ and $2^{nd}$ logarithmic derivatives are −0.5 and 0, respectively. For a temporally extended pulse produced by the one or more illumination sources 12, the early post-heating logarithmic temperature-time behavior is perturbed before it eventually converges to the instantaneous solution after a settling period. The OEIR-NDT active thermography system 10 corrects for the extended pulse perturbation, so that the temperature increase of the surface, $T_S$, of the test piece, T, during the settling period is compensated for, and the step heated derivative response appear to be identical to that of instantaneous heating. To do this, a function describing the response of a material to a temporally extended pulse produced by the one or more illumination sources 12 is generated by convolving the signal of the actual input pulse with the ideal delta response used in the TSR method. The ratio of this derived function to the known delta response can then be used to generate a correction factor, $T_{corr}(t)$, that can be applied to the acquired raw data, $T_{raw}(t)$ (which may be based upon the frame rate of the images captured by the IR camera 14; the selected frame rate may be related to the test piece, T, because the amount of frame to be captured may be dependent upon the depth test piece, T). In the simplest case of a rectangular pulse centered at t=0 with finite duration $\tau$, the surface temperature at any time, t, after the pulse has completed, $T_{raw}(t)$ |t>$\tau$/2, can be corrected for by applying the following equation:

$$T_{corr}(t) = \frac{T_{raw}(t)}{2\sqrt{t} * \left( \sqrt{t + \frac{\tau}{2}} - \sqrt{t - \frac{\tau}{2}} \right)}$$

wherein: $\tau$=duration of illumination pulse (seconds)

The OEIR-NDT active thermography system 10 also applies a similar correction for the effects of convection, which may become considerable if the surface, $T_S$, of the test piece, T, is heated significantly above room temperature and data acquisition period becomes relatively long. Both conditions are likely to apply to certain test pieces, T, such, as, for example, thick polymer composite structures such as those found in wind turbine components. Convection is described by Newton's law of cooling $$\frac{dQ}{dt} = h * A(T(t) - T_{env}) = -h * A\Delta T(t)$$

where:
(1) Q is the thermal energy,
(2) t is time,
(3) A is the surface area to which heat is transferred, (4) T is the temperature of the object,
(5) $T_{env}$ is the temperature surrounding environment, and
(6) h is the heat transfer coefficient—a constant that relates to the heat absorption rate of the fluid surrounding the sample (typically air, for NDT applications), and relatively independent of the temperature difference between the test piece, T, and the environment. Newton's law states that the rate of heat loss of a body is proportional to the difference in temperatures between the body and its surroundings.

In the OEIR-NDT active thermography system 10, conduction is typically the dominant cooling mechanism. However, as the temperature of the surface, $T_S$, of the test piece, T, decreases due to conduction, convection begins to play a more significant role. In a given experiment, we can estimate the time $t_{conv}$ at which the effects of convection become comparable to conduction cooling. The OEIR-NDT active thermography system 10 does this by providing an electronic thermometer (not shown) that is connected to the computing resource 16 in order to measure ambient air temperature and comparing that temperature to the temperature of the surface, $T_S$, of the test piece, T, at a particular time after heating. From these two temperatures, and knowledge of Q and h, which can be estimated from tabulated values, the computing resource 16 can integrate Newton's law and calculate $t_{conv}$. For experiments where the duration of data acquisition is less than $t_{conv}$, the computing resource 16 may ignore convection effects. However, for longer durations, the computing resource 16 can compensate for convection losses. Referring to FIGS. 3A-3B and 4A-4B, the net effect of the correction is that the extended pulse response more closely resembles that of delta function excitation.

Convection Correction

Ideal: $T(t) \times Q/\sqrt{s\pi t} - T_{pre}$

Detected: $T_{det} = (T(t) + T_{amb})e^{-ht}$

;normal assumption is that $T_{amb} = T_{pre}$
;camera detects absolute sample temp Corrected: $T(t) = T_{det} e^{ht} - T_{amb}$ Reduces to ideal case when $T_{amb} = T_{pre}$ & h=0
Remains active when $T_{amb} = T_{pre}$ but h≠0 ($T_{pre}$ drives convection since final temp >$T_{pre}$)
Wherein:
Q=thermal energy
t=time
T(t)=test piece temperature at time t
$T_{det}$=surface temperature of the test piece, T, immediately after excitation
$T_{amb}$=ambient temperature of the fluid surrounding the test piece, T, immediately prior to excitation
h=heat transfer coefficient of the test piece
$T_{pre}$=surface temperature of the test piece, T, immediately prior to excitation
For best experimental results, convection effects should be negligible for t<2.5t*
For $T_{amb}$=0

$$T_{det} = T(t)e^{-ht}$$

$$\frac{T(t)}{T_{det}} = e^{ht}$$

$$\frac{T(2.5 \cdot t^*)}{T_{det}} = e^{h2.5t^*} < M \quad (M = \text{acceptable error limit})$$

For a given h, we can use the equation above to determine the duration for which convection losses are negligible. For best experimental results, convection losses should be negligible for t<2.5t*. The duration of an experiment should be 2 to 3 times as long as t*, wherein t* is the time required to reach the deepest interface of interest within test piece, T.

Background/Emissivity Correction

Ideal: $T(t) = \dfrac{Q}{e\sqrt{\pi t}} - T_{pre}$

Detected: $T_{det} = \varepsilon T(t) + (1 - \varepsilon)T_{bkgd}$

Corrected: $T(t) = \dfrac{T_{det} - (1 - \varepsilon)T_{bkgd}}{e}$

Combined Convection and Background/Emissivity Correction $$T(t) = \frac{T_{det}e^{ht} + T_{amb} - (1 - e)T_{bkgd}}{e}$$

As described above at FIGS. 1A-1D, the computing resource 16 may be communicatively coupled to each of the one or more illumination sources 12, the infrared (IR) camera 14, the at least one second reflector 20, the display 22 and the user interface 24. Further, as seen in FIGS. 1A-1D, all of the components (e.g., the one or more illumination sources 12, the infrared (IR) camera 14, the computing resource 16, the at least one first reflector 18, the at least one second reflector 20, the display 22, the user interface 24, the motor 30, and the axle 32) may be structurally connected (by way of, for example, brackets, fasteners or the like) to a support structure 34. In some instances, the support structure 34 may be disposed upon an underlying ground surface, G. In some instances, the OEIR-NDT active thermography system 10 may be designed to be small enough such that the support structure 34 defines a housing that may be held by a technician.

Figure 5A:
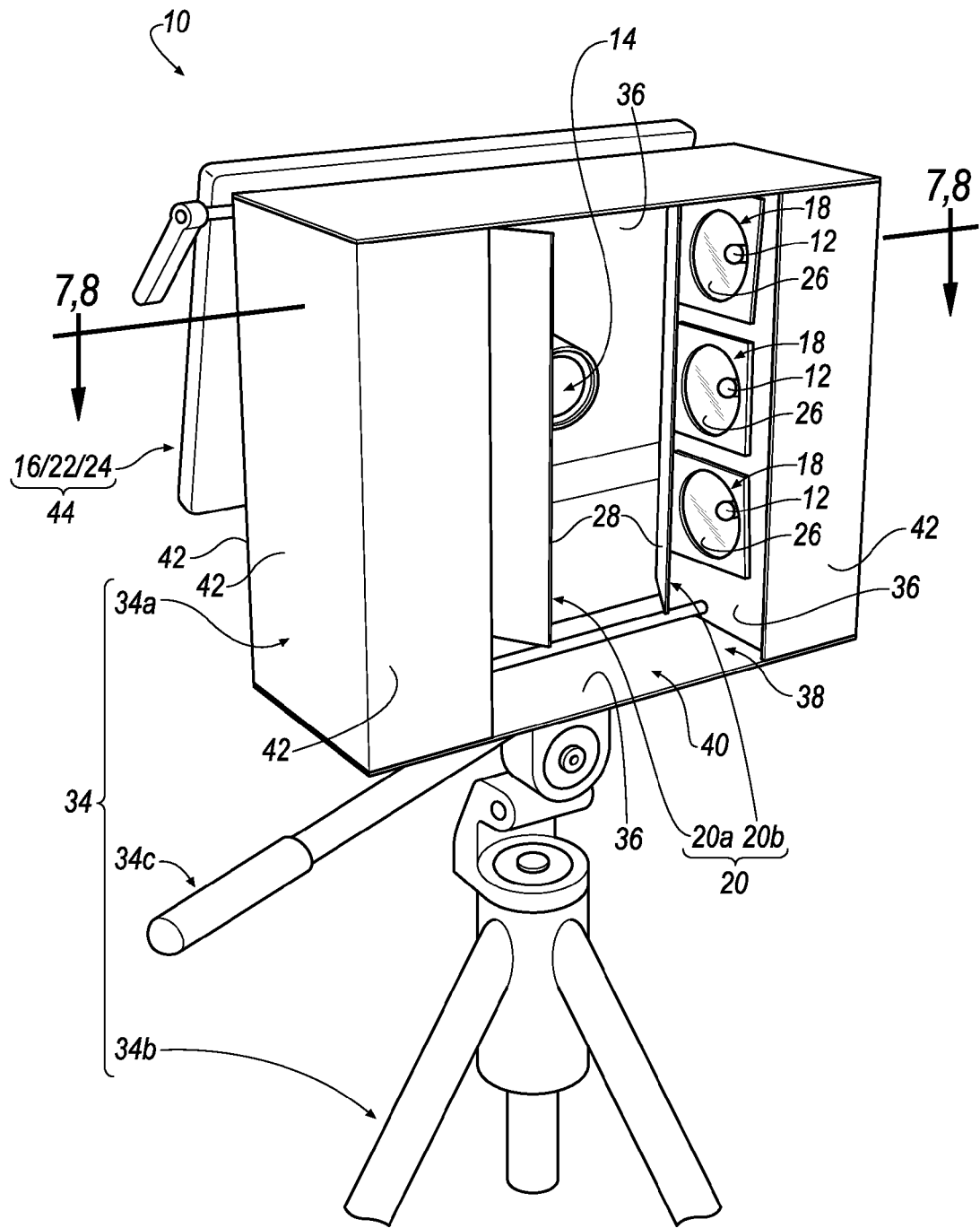
FIG. 5A is a front perspective view of an exemplary OEIR-NDT active thermography system.
Figure 5B:
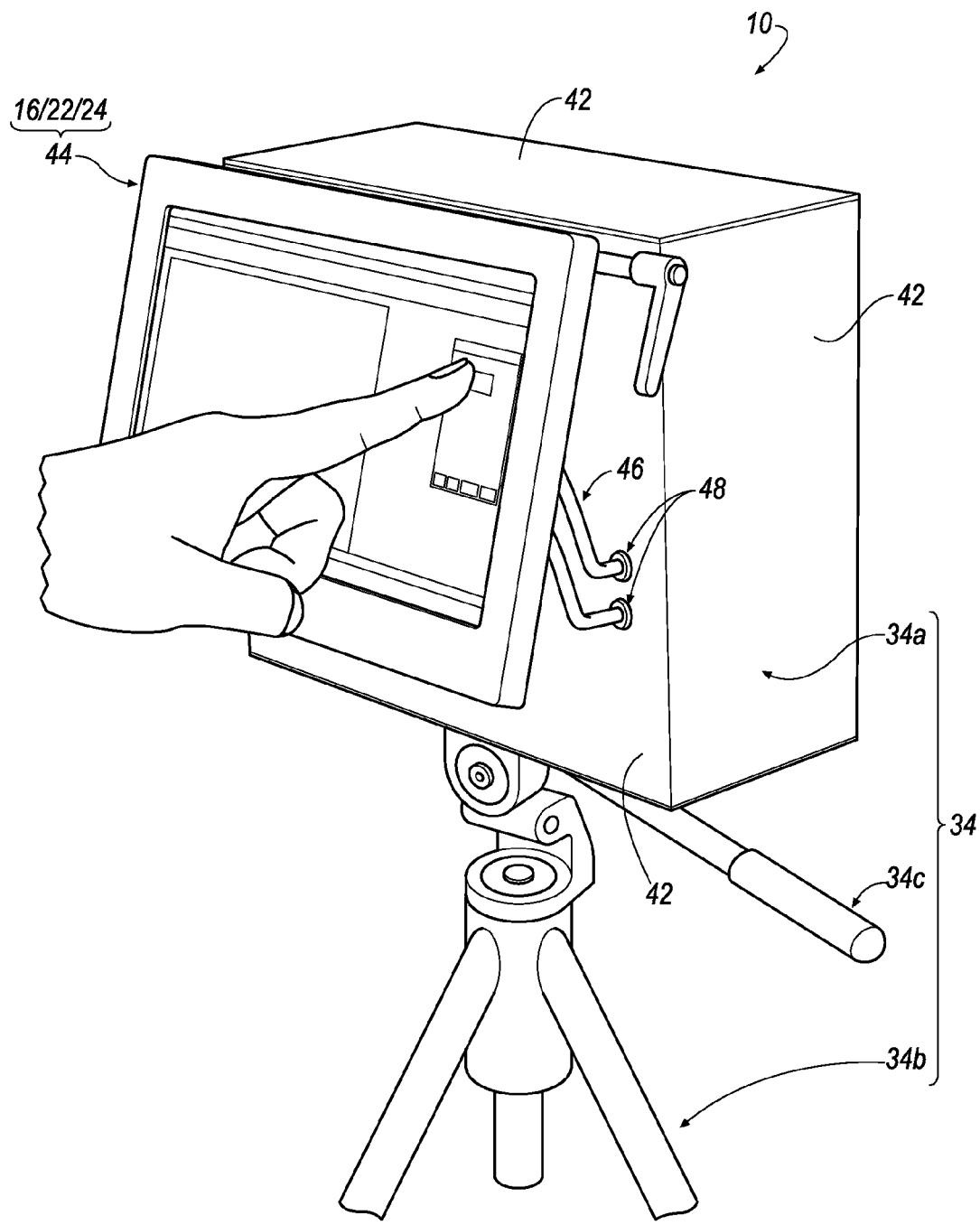
FIG. 5B is a rear perspective view of the OEIR-NDT active thermography system of FIG. 5A.
Figure 6:
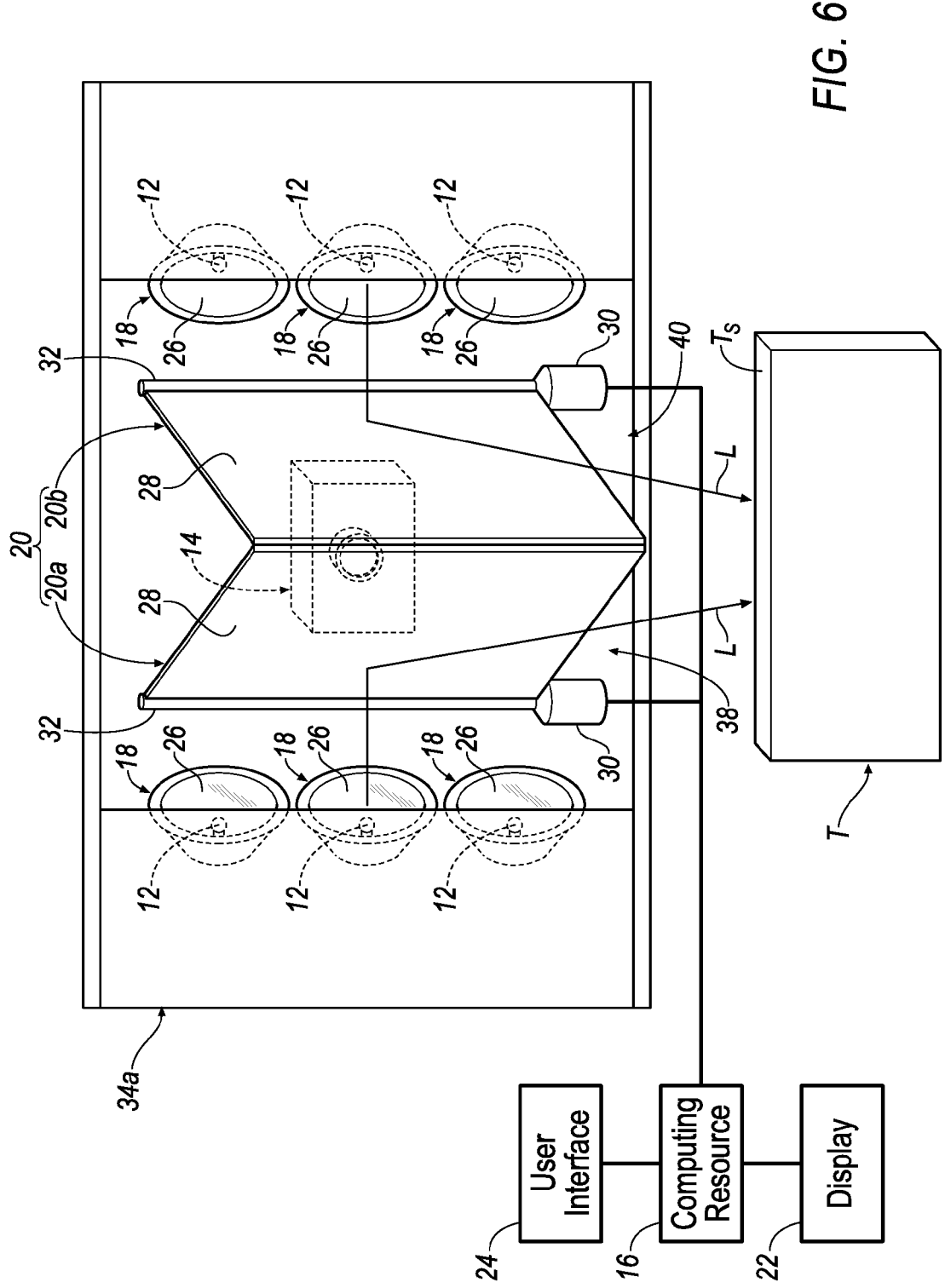
FIG. 6 is a front view of the OEIR-NDT active thermography system of FIG. 5A.

Referring to FIGS. 5A-5B and 6, an exemplary embodiment of the OEIR-NDT active thermography system 10 is shown where: (1) the one or more illumination source 12 includes six illumination sources 12, (2) the at least one second reflector 20 includes a left second reflector 20a and a right second reflector 20b, and (3) the support structure 34 includes a housing portion 34a, a pod portion (e.g., a tripod) 34b and an adjuster portion 34c that permits the housing portion 34a to be adjusted (e.g., pivoted, rotated and/or pitched) relative to the pod portion 34b.

The housing 34a includes a plurality of interior walls 36 defining a recessed cavity 38. The one or more illumination sources 12, the IR camera 14 and the at least one second reflector 20 are positioned within the recessed cavity 38 and may be connected to one or more of the plurality of interior walls 36. Access to the recessed cavity 38 is permitted by an opening 40 (see also, e.g., FIGS. 1A-1D). The test piece, T, may be arranged in an opposing relationship with respect to the opening 40 in order to: (1) permit the at least one second reflector 20 to reflect the one or more beams or rays of light, L, emitted from the one or more illumination sources 12 toward the surface, $T_S$, of the test piece, T, and (2) permit the IR camera 14 to image the surface, $T_S$, of the test piece, T, after the surface, $T_S$, of the test piece, T, has been heated by the reflected one or more beams or rays of light, L.

Referring to FIGS. 5A and 5B, the housing 34a may also be defined by a plurality of exterior walls 42. As seen in FIG. 5B, the computing resource 16, the display 22 and the user interface 24 may be integrated into a single device such as, for example, a tablet computer. Instead of a table computer, a compact PC can be used in conjunction with a touch screen/display. A small PC can easily be packaged along with the drive electronics for the motors and control circuitry in the same housing 34a (the entire unit is the size of a cigar box). A PC is more easily upgraded and maintained than a tablet computer, and the touch screen is lighter and generates less heat than a tablet computer. Also, the PC processor is more powerful than the tablet computer, and allows the TSR operations (i.e. post processing of collected data) to be performed efficiently and quickly. The tablet computer 44 may be mounted to a rear exterior wall 42 of the plurality of exterior walls 42 of the housing 34a. The tablet computer 44 may be communicatively coupled to the one or more illumination sources 12, the IR camera 14 and motor 30 by way of cables or communication conduits 46 that extend through one or more passages 48 formed in one or more of the exterior walls 42 of the housing 34a.

Referring to FIG. 6, a front view of the OEIR-NDT active thermography system 10 of FIGS. 5A-5B is shown. A first column of three light sources 12 of the six light sources 12 are arranged within the recessed cavity 38 proximate the left second reflector 20a of the two second reflectors 20. A second column of three light sources 12 of the six light sources 12 are arranged within the recessed cavity 38 proximate the right second reflector 20b.

Figure 7A:
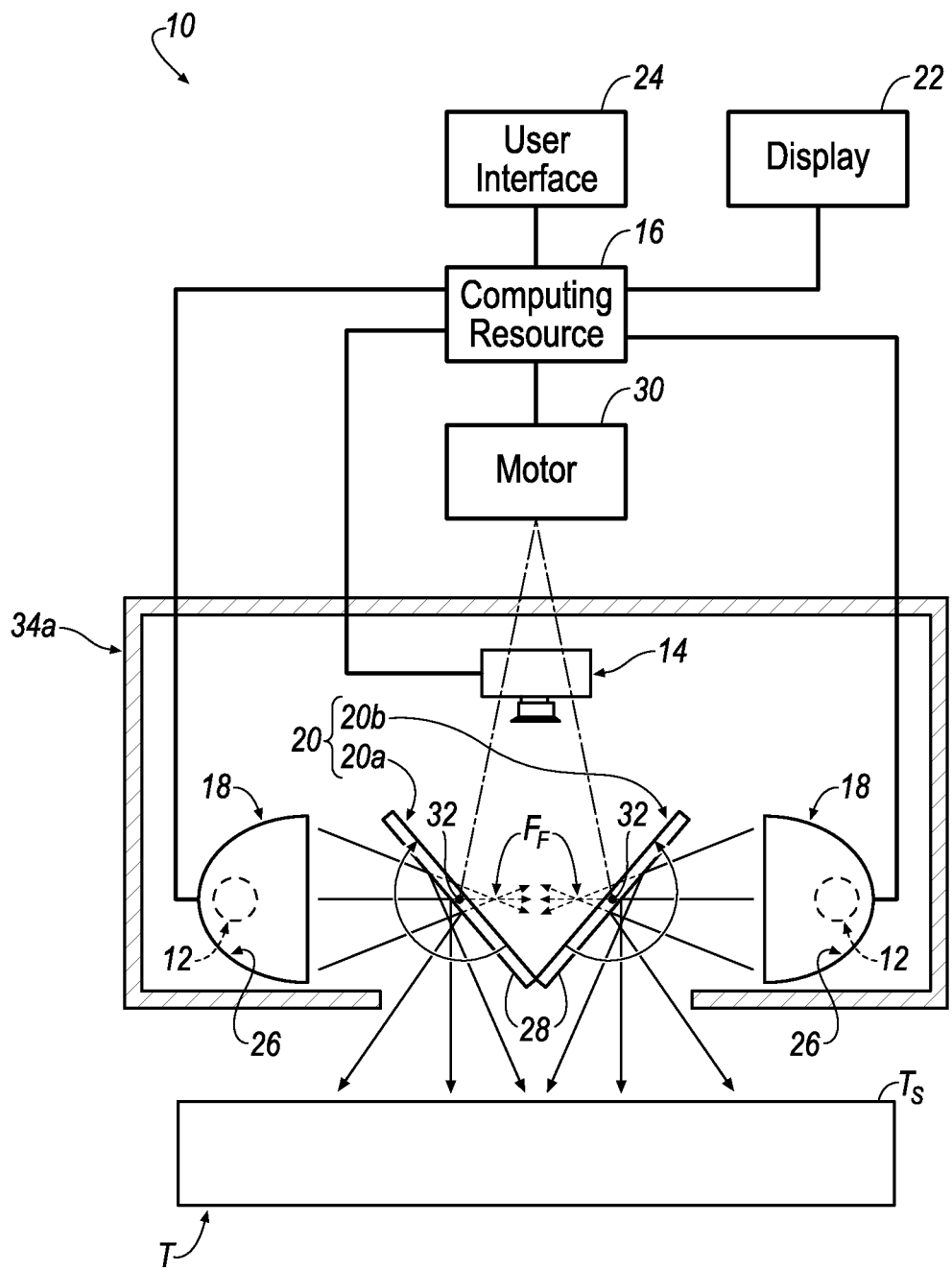
FIG. 7A is a view of the OEIR-NDT active thermography system according to line 7,8-7,8 of FIG. 5A.
Figure 7B:
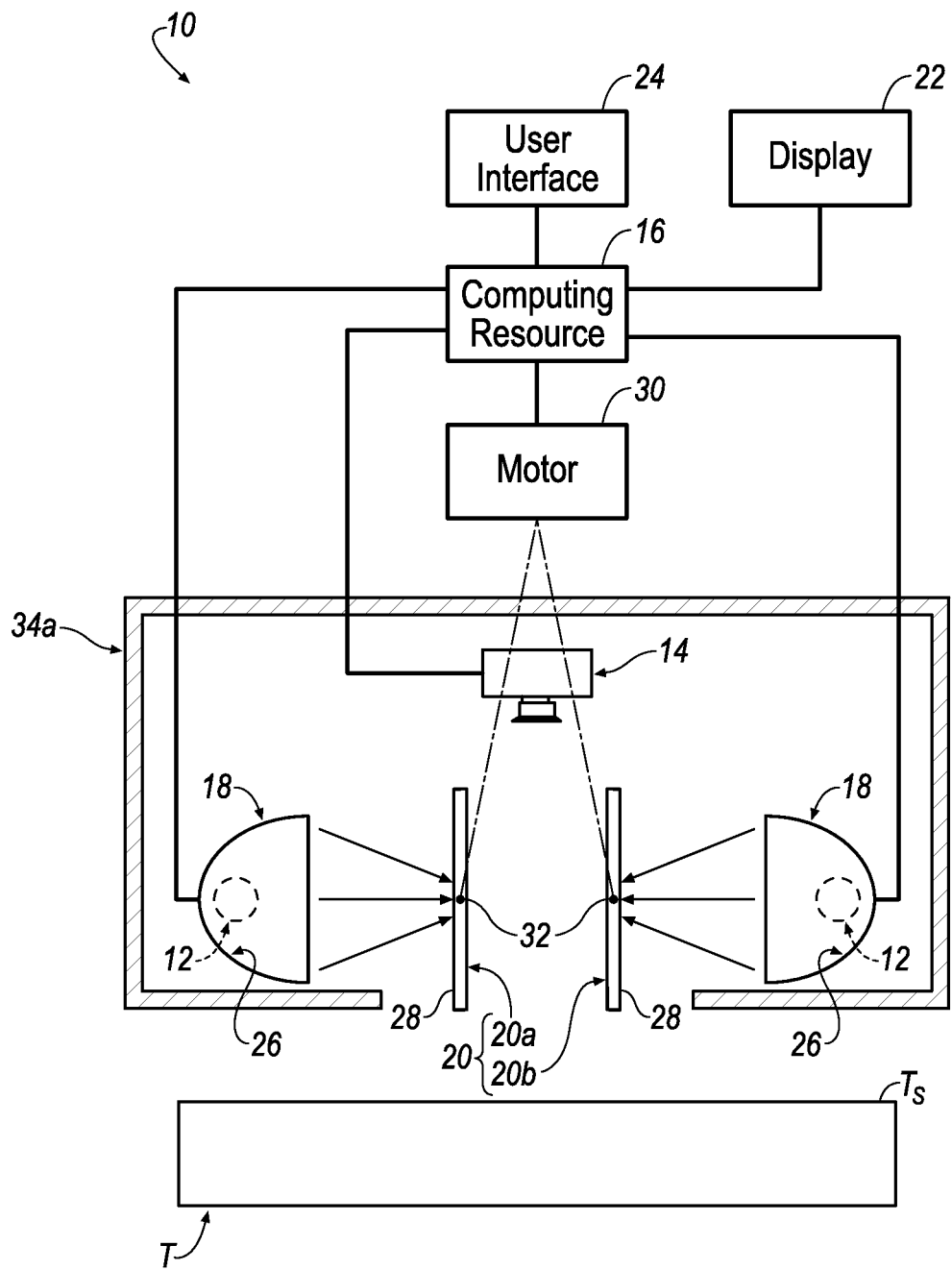
FIG. 7B is another view of the OEIR-NDT active thermography system according to line 7,8-7,8 of FIG. 5A.

As seen in FIGS. 6 and 7A, the left second reflector 20a and the right second reflector 20b are shown spatially manipulated to the "open position" (as similarly described above and as seen in, e.g., FIG. 1B). Referring to FIG. 7B, the left second reflector 20a and the right second reflector 20b are spatially manipulated to the "closed position" (as similarly described above and as seen in FIG. 1C).

When the left second reflector 20a and the right second reflector 20b are arranged in the "open position" as seen in FIGS. 6 and 7A, the left second reflector 20a and the right second reflector 20b reflect the one or more beams or rays of light, L, over substantially all of a target area of the surface, $T_S$, of the test piece, T. Further, when the left second reflector 20a and the right second reflector 20b are arranged in the "open position," the left second reflector 20a and the right second reflector 20b provide a second function by being arranged in front of IR camera 14 for the purpose of "blocking" or shielding the lens of the IR camera 14 when the surface, $T_S$, of the test piece, T, is being heated by the one or more beams or rays of light, L, in order to protect the lens and overall body of the IR camera 14 from being heated. If the left second reflector 20a and the right second reflector 20b did not block or shield the IR camera 14 as described above, the lens or detector of an IR camera 14 may be heated and internal electronic noise in the camera may increase, thereby resulting in a spatial pattern being superimposed on the image of the object field.

When the left second reflector 20a and the right second reflector 20b are arranged in the "closed position" as seen in FIG. 7B, the left second reflector 20a and the right second reflector 20b may "block" or reflect the one or more beams or rays of light, L, back toward the at least one first reflector 18 such that none of the one or more beams or rays of light, L, are reflected over substantially all of a target area of the surface, $T_S$, of the test piece, T (i.e., no energy associated with the one or more beams or rays of light, L, reaches the surface, $T_S$, of the test piece, T; this eliminates the possibility of IR radiation from the warm lamps or associated hardware impinging on the IR camera lens directly, or onto the sample surface and then being reflected off of the sample surface into the IR camera lens. Toward this end, the left second reflector 20a and the right second reflector 20b may be constructed with a double wall (e.g., a pair of walls with an insulator disposed there between such as, for example, air), so that the once the left second reflector 20a and the right second reflector 20b are warmed, the left second reflector 20a and the right second reflector 20b do not radiate heat toward the surface, $T_S$, of the test piece, T). Additionally, when the left second reflector 20a and the right second reflector 20b are arranged in the "closed position", the IR camera 14 is permitted to have an unobstructed sightline to the sample surface while also being shielded from the one or more illumination sources 12.

As seen in FIGS. 8A-8D, the left second reflector 20a and the right second reflector 20b may be spatially manipulated in a manner to be actively adjusted between a range of angles, $\theta_A$ (e.g. between approximately 0° as similarly seen in FIG. 1A and 90° as similarly seen in FIG. 1C). When arranged between the range of angles, $\theta_A$, the left second reflector 20a and the right second reflector 20b may, for example, be spatially adjusted in an oscillating manner, in order to actively reflect the one or more beams or rays of light, L, at all or selected portions of a target area of the surface, $T_S$, of the test piece, T.

Figure 8A:
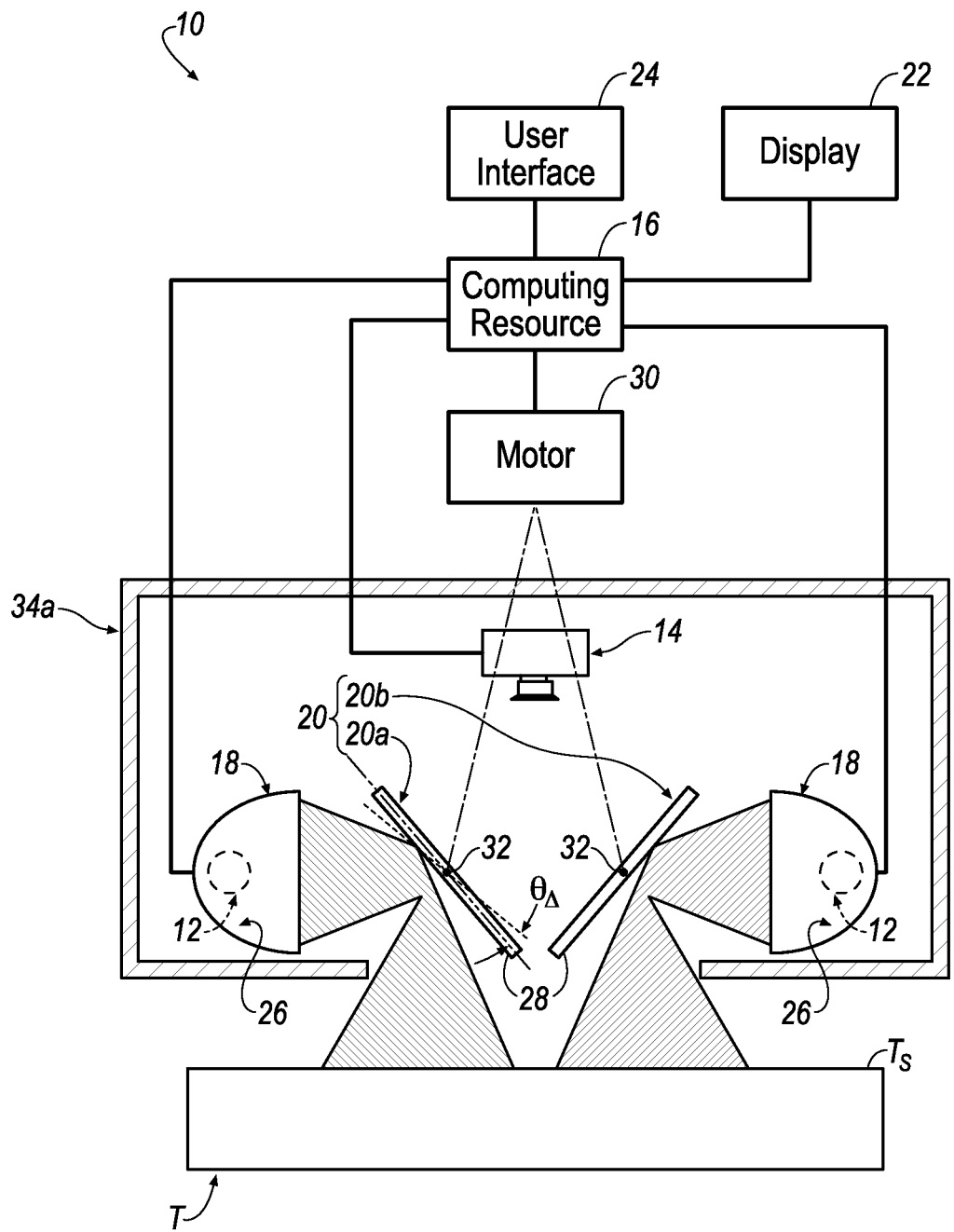
FIG. 8A is another view of the OEIR-NDT active thermography system according to line 7,8-7,8 of FIG. 5A.
Figure 8B:
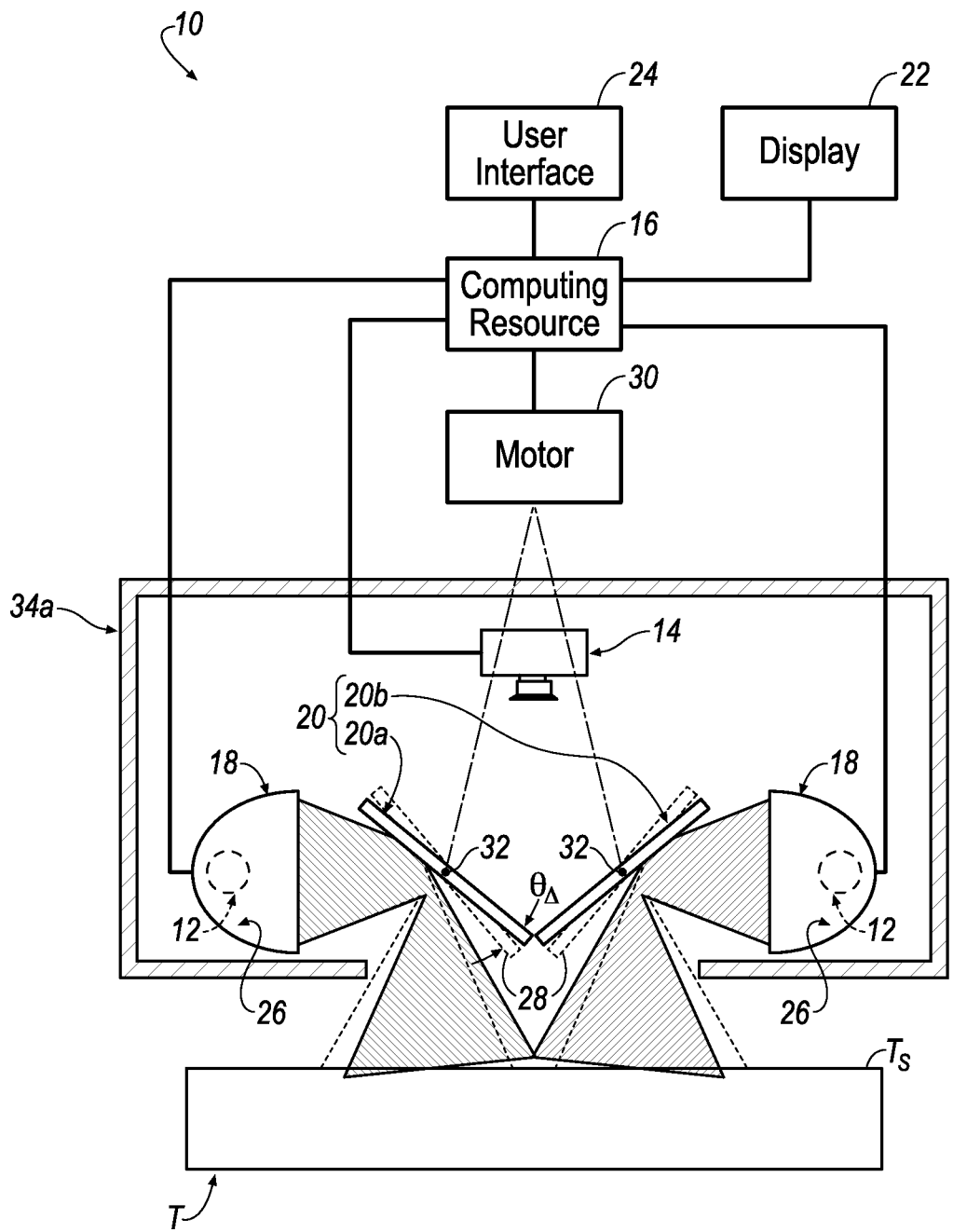
FIG. 8B is another view of the OEIR-NDT active thermography system according to line 7,8-7,8 of FIG. 5A.

Unlike the exemplary embodiment of the OEIR-NDT active thermography system 10 described at FIGS. 6 and 7A7B, the oscillating movement of the left second reflector 20a and the right second reflector 20b of the exemplary embodiment of the OEIR-NDT active thermography system 10 described at FIGS. 8A-8B permits the one or more beams or rays of light, L, to be adjusted during the heating of the surface, $T_S$, of the test piece, T. Such movement of the left second reflector 20a and the right second reflector 20b permits the one or more beams or rays of light, L, to "paint" or scan over a region of the surface, $T_S$, of the test piece, T, by way of the oscillating motion of the left second reflector 20a and the right second reflector 20b. The oscillating movement of the left second reflector 20a and the right second reflector 20b allows the OEIR-NDT active thermography system 10 to control the overlap between adjacent beams of the one or more beams or rays of light, L, to avoid generation of hot or cold spots on the surface, $T_S$, of the test piece, T, and, as a result, uniformity is improved upon. The oscillating movement of the left second reflector 20a and the right second reflector 20b also blurs features of the filament or arc of the one or more illumination sources 12 that may be imaged onto the surface, $T_S$, of the test piece, T. Since the focus of the one or more beams or rays of light, L, is slightly before or after the open position of the left second reflector 20a and the right second reflector 20b, a small oscillating motion of the left second reflector 20a and the right second reflector 20b can result in significant motion in the far field.

Figure 9:
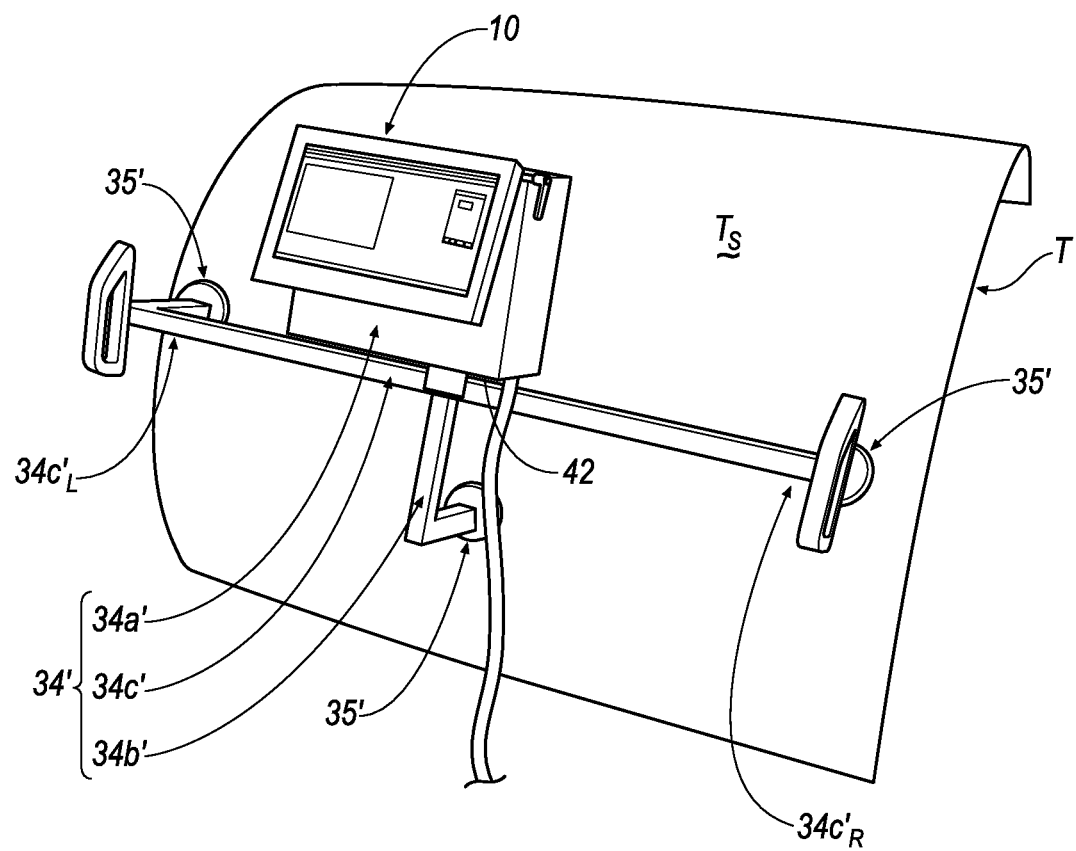
FIG. 9 is a rear perspective view of an exemplary OEIR-NDT active thermography system.

Referring to FIG. 9, another exemplary support structure 34' is shown. The support structure 34' may be connected to the OEIR-NDT active thermography system 10 shown and described above in FIGS. 5A-8B where: (1) the one or more illumination sources 12 includes six illumination sources 12 and (2) the at least one second reflector 20 includes a left second reflector 20a and a right second reflector 20b.

The support structure 34' includes a housing portion 34a' that is substantially similar to the housing portion 34a described above. The support structure 34', however, does not include a pod portion (e.g., a tripod) 34b and an adjuster portion 34c that permits the housing portion 34a to be adjusted (e.g., pivoted, rotated and/or pitched) relative to the pod portion 34b. Rather, the support structure 34' includes a leg portion 34b' and a linear guide bar 34c'. In some examples, the leg portion 34b' may include an "L" shape and extends from a lower exterior wall 42 of the housing portion 34a'. One or both of the leg portion 34b' and the linear guide bar 34c' may bear the weight of the housing portion 34a' that may contain and/or support the OEIR-NDT active thermography system 10.

Each of the leg portion 34b' and the linear guide bar 34c' may include one or more suction cups 35'. The one or more suction cups 35' permits the support structure 34' to be removably-attached to the surface, $T_S$, of the test piece, T, as opposed to being arranged upon the pod portion 34b, which may be disposed upon an underlying ground surface, G.

In some instances, the linear guide bar 34c' may remain removably-fixed upon the surface, $T_S$, of the test piece, T, by way of the one or more suction cups 35' extending therefrom. When a plurality of areas of the surface, $T_S$, of the test piece, T, are investigated by the OEIR-NDT active thermography system 10, a technician may linearly adjust a position of the housing portion 34a' along the linear guide bar 34c' (e.g., from a left-most end $34c'_L$ of the linear guide bar 34c' to a right-most end $34c'_R$ of the linear guide bar 34c') by successively removably-attaching the suction cup 35' of the leg portion 34b' to surface, $T_S$, of the test piece, T, from a first location upon the surface, $T_S$, of the test piece, T, proximate the left-most end $34c'_L$ of the linear guide bar 34c' to an $n^{th}$ location upon the surface, $T_S$, of the test piece, T, proximate the right-most end $34c'_R$ of the linear guide bar 34c'.

When the suction cup 35' of the leg portion 34b' is successively removably-attached to surface, $T_S$, of the test piece, T, the leg portion 34b' may contact or be controllably-interfaced with the linear guide bar 34c'. For example, cooperation of the leg portion 34b' and the linear guide bar 34c' in such a manner may provide the benefit of repeatably-controlling a spacing or distance between the lens of the IR camera 14 and the surface, $T_S$, of the test piece, T.

Figure 10:
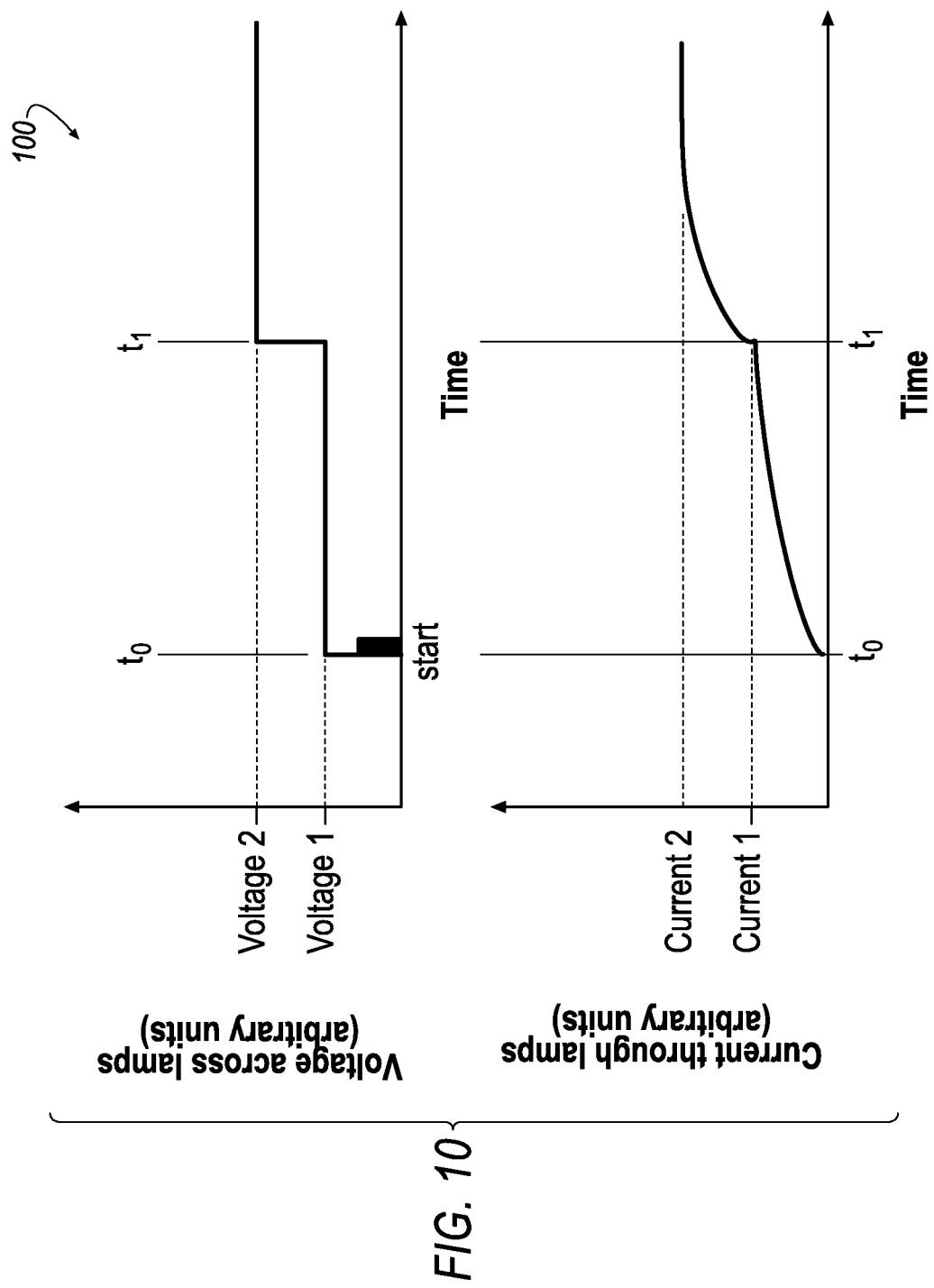
FIG. 10 is an exemplary timing diagram illustrating application of a voltage to the one or more illumination sources of any of the OEIR-NDT active thermography systems of FIGS. 1A-1D, 5A-8B and 9.

FIG. 10 illustrates an exemplary voltage timing diagram 100 relating to application of a voltage to the one or more illumination sources 12 where: (1) $t_0$ is a time when a first voltage ("Voltage 1") is applied to the one or more illumination sources 12, (2) $t_1$ is a time when a second voltage ("Voltage 2") is applied to the one or more illumination sources 12, and (3) the first voltage ("Voltage 1") is less than the second voltage ("Voltage 2"). When a voltage is applied to the one or more illumination sources 12 (at, e.g., time=$t_0$), there may be a significant delay before steady state light output is achieved. Because the one or more illumination sources 12 may be sensitive to in-rush currents at start-up, the one or more illumination sources 12 may experience a shortening of their life expectancy or may be damaged by an initial current surge. Therefore, to protect the one or more illumination sources 12, a low voltage (e.g. ½ to ¾ of the illumination sources rated voltage) is initially applied to the one or more illumination sources 12. Subsequently (at, e.g., time=$t_1$), a higher voltage (e.g., the second voltage, "Voltage 2") is applied to the one or more illumination sources 12 after a predetermined time laps ($t_1-t_0$), such as 0.5 seconds, allowing the current to reach its ultimate "working range. In order to optimize a heating cycle for heating the surface, $T_S$, of the test piece, T, the at least one second reflector 20 is not moved to the "open position" (as seen in, e.g., FIGS. 1B, 1D, 6, 7A, 8A-8B) until the current reaches a designated threshold level.

Figure 11:
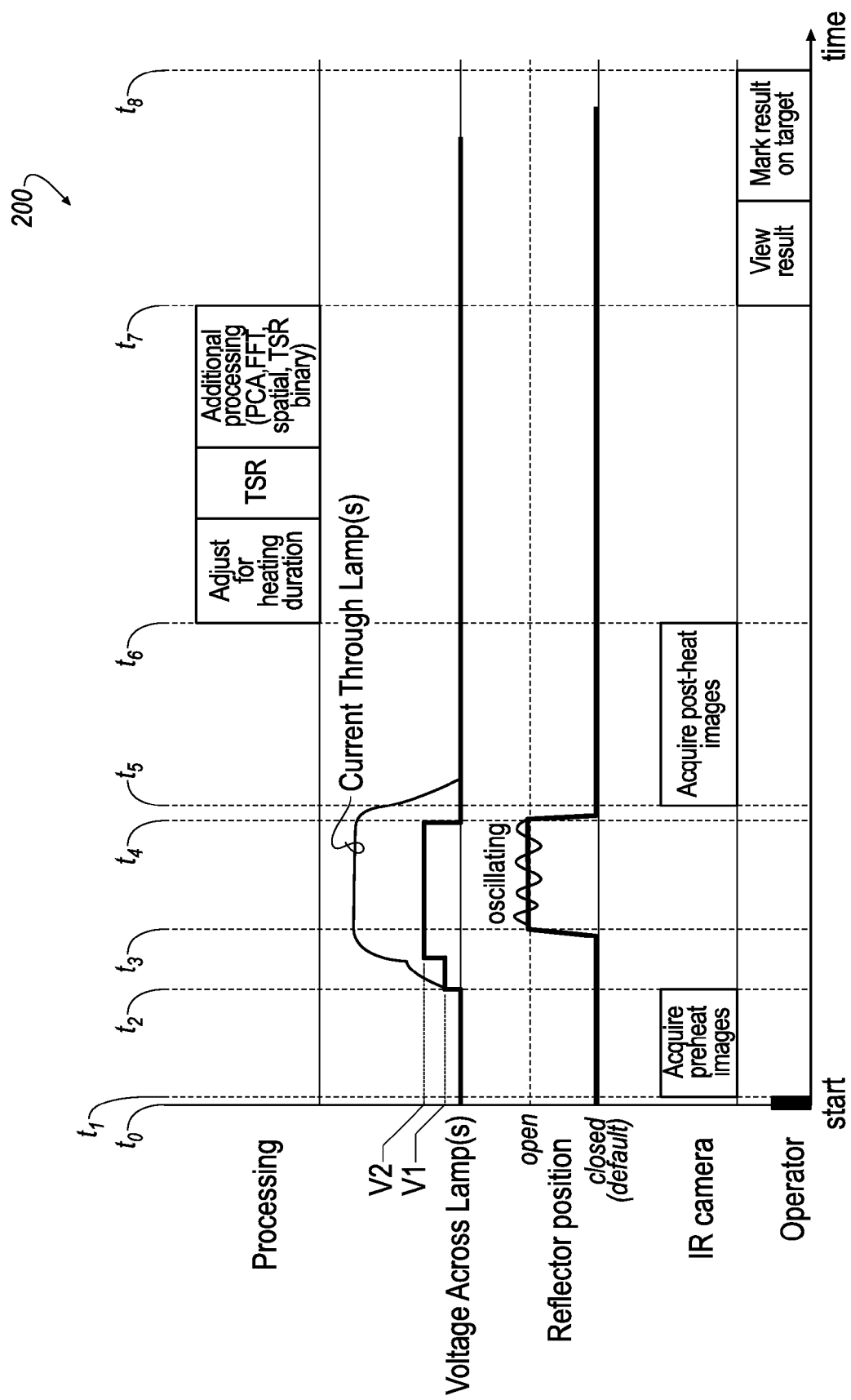
FIG. 11 is an exemplary timing diagram illustrating a method for operating any of the OEIR-NDT active thermography systems of FIGS. 1A-1D, 5A-8B and 9.

FIG. 11 illustrates an exemplary system timing diagram 200 for timing the operation of the OEIR-NDT active thermography system 10 illustrating successive instances of time from a first instance of time, $t_0$, to a last instance of time, $t_8$. At time, $t_0$, a methodology associated with the system timing diagram 200 is initiated. Initiation of the methodology may commence upon a user selecting or pressing a "start button" on the user interface 24.

From time, $t_0$, to time, $t_1$, nothing may happen as the OEIR-NDT active thermography system 10 may be initiating. Then, from time, $t_1$, to time, $t_2$, the IR camera 14 may acquire images of the surface, $T_S$, of the test piece, T, prior to the surface, $T_S$, of the test piece, T, being heated by the reflected one or more beams or rays of light, L, impinging upon the surface, $T_S$, of the test piece, T.

Then, from time, $t_2$, to time, $t_4$, the first voltage and then the second voltage may be applied to the one or more illumination sources 12 as described above at FIG. 10. At time, $t_3$, which occurs between a period of time defined by the times, $t_2$ and $t_4$, the at least one second reflector 20 may be oscillated (i.e. swept back and forth), $\theta_A$, as described above. Oscillation of the at least one second reflector 20 may occur between a period of time defined by the times, $t_3$ and $t_4$.

At time, $t_4$, the second, high voltage applied to the one or more illumination sources 12 is ceased along with the oscillation of the at least one second reflector 20. For a period of time defined by the times, $t_4$ and $t_5$, the at least one second reflector 20 may be spatially manipulated from the "open position" to the "closed position"; once the at least one second reflector 20 is arranged in the "closed position," at time, $t_5$, the IR camera 14 is actuated in order to acquire images of the surface, $T_S$, of the test piece, T, after the surface, $T_S$, of the test piece, T, has been heated by the reflected one or more beams or rays of light, L, impinging upon the surface, $T_S$, of the test piece, T, as a result of the at least one second reflector 20 reflecting the one or more beams or rays of light, L, in an oscillating manner as described above between a period of time defined by the times, $t_3$ and $t_4$. The IR camera 14 captures images of the surface, $T_S$, of the test piece, T, between a period of time defined by the times, $t_5$ and $t_6$.

Then, between a period of time defined by the times, $t_6$ and $t_7$, the computing resource 16 processes the images captured by the IR camera 14. The processing may include utilization of the Thermographic Signal Reconstruction (TSR) method as well as further adjustments when an extended, rather than instantaneous excitation of the one or more illumination sources 12 is used (e.g., one such adjustment, as described above in FIG. 2, is to shift the time assigned to each collected frame produced by the IR camera 14 so that time t=0 indicates the midpoint of the heating period of the surface, $T_S$, of the test piece, T). Other processing may include Principal Component Analysis (PCA), Fast Fourier Transform (FFT) and Thermographic Signal Reconstruction (TSR) Binary.

Then, between a period of time defined by the times, $t_7$ and $t_8$, the processed image may be displayed upon the display 22 where a technician can view the processed image. The technician may then mark-up the displayed image by, for example, touching the display 22 and dragging his/her finger across the display 22 if, for example, the display 22 is a portion of a tablet computer 44. By permitting the displayed image to be marked-up, the technician may create notes on the displayed image or draw attention to discovered imperfections of the test piece, T, which may include, for example, water trapped in a composite sandwich structure of the test piece, T.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. An assembly, comprising:
    an optically excited infrared nondestructive testing active thermography system including:
        one or more illumination sources;
        at least one first reflector arranged about the one or more illumination sources, wherein the at least one first reflector has a near focal point and a far focal point, wherein the one or more illumination sources is/are positioned at least proximate the near focal point of the at least one first reflector;
        at least one second reflector positioned at least proximate the far focal point; and
        a computing resource communicatively-coupled to a motor that is coupled to the at least one second reflector for manipulating the at least one second reflector between at least:
            a first spatial orientation, and
            a second spatial orientation, wherein at least one of the first spatial orientation and the second spatial orientation results in the at least one second reflector reflecting light that originates from the one or more illumination sources, wherein the light is directed toward the at least one second reflector as a result of the light being:
                directly propagated from the one or more illumination sources, and
                reflected by the at least one first reflector.

2. The assembly according to claim 1, wherein the system further includes:
    an infrared camera communicatively-coupled to the computing resource, wherein positioning of the at least one second reflector in the first spatial orientation results in:
        the light being substantially directly and indirectly blocked by the at least one second reflector such that the light is not incident upon or detected by the infrared camera while
        the light is reflected by the at least one second reflector toward a surface of a test piece.

3. The assembly according to claim 2, wherein the system further includes:
    an infrared camera communicatively-coupled to the computing resource, wherein positioning of the at least one second reflector in the second spatial orientation results in:
        the infrared camera detecting heat from the surface of the test piece that was heated as a result of the light that was reflected by the at least one second reflector toward the surface of the test piece while
        heat emanating from one or more of the one or more illumination sources and the at least one first reflector is blocked by the at least one second reflector such that the heat emanating from one or more of the one or more illumination sources and the at least one first reflector is not incident upon or detected by the infrared camera.

4. The assembly according to claim 2, further comprising:
    a support structure that is connected to and supports one or more of the one or more illumination sources, the infrared camera, the at least one first reflector, the at least one second reflector, the computing resource and the motor.

5. The assembly according to claim 4, wherein the support structure includes a housing portion that is connected to and supports one or more of: the one or more illumination sources, the infrared camera, the at least one first reflector, the at least one second reflector, the computing resource and the motor.

6. The assembly according to claim 5, wherein the housing portion includes:
    a plurality of interior walls, and
    a plurality of exterior walls, wherein the plurality of interior walls defines a recessed cavity, wherein one or more of the one or more of the one or more illumination sources, the infrared camera, the at least one first reflector, the at least one second reflector is/are disposed within the recessed cavity.

7. The assembly according to claim 6, wherein the one or more illumination sources includes:
    a first column of illumination sources, and
    a second column of illumination sources, wherein a first reflector of the at least one first reflector is arranged about each illumination source forming the first column of illumination sources and the second column of illumination sources.

8. The assembly according to claim 7, wherein the at least one second reflector includes:
    a left second reflector, and
    a right second reflector, wherein the first column of illumination sources are arranged proximate the left second reflector, wherein the second column of illumination sources are arranged proximate the right second reflector.

9. The assembly according to claim 6, further comprising:
a display connected to the computing resource; and
a user interface connected to the computing resource, wherein one or more of the computing resource, the display and the user interface is/are disposed upon one of the plurality of exterior walls of the housing portion.

10. The assembly according to claim 6, wherein the computing resource is a tablet computer, wherein the tablet computer also includes a display and a user interface, wherein the tablet computer is disposed upon one of the plurality of exterior walls of the housing portion.

11. The assembly according to claim 5, wherein the support structure further includes:
a pod portion connected to the housing portion.

12. The assembly according to claim 11, wherein the support structure further includes:
an adjuster portion that connects the housing portion to the pod portion, wherein the adjuster portion permits the housing portion to be pivoted, rotated and/or pitched relative to the pod portion.

13. The assembly according to claim 5, wherein the support structure further includes:
a leg portion connected to the housing portion, and
a linear guide bar connected to one or both of the leg portion and the housing portion, wherein one or more of the leg portion and the linear guide bar includes one or more suction cups to permit one or more of the leg portion and the linear guide bar to be removably-attached to the surface of the test piece.

14. The assembly according to claim 2, wherein the at least one first reflector is arranged relative to the surface of the test piece such that the light is not directed toward the surface of the test piece but rather parallel to the surface of the test piece.

15. The assembly according to claim 2, wherein the system further includes:
an electronic thermometer connected to the computing resource, wherein the electronic thermometer measures ambient air temperature, wherein the computing resource compares the comparing the ambient temperature to a detected temperature of the surface of the test piece.

16. A method for operating the system of claim 2, comprising:
arranging the one or more illumination sources and the at least one first reflector in a spatially fixed orientation;
directing the light along a path that is substantially parallel to the surface of the test piece;
spatially manipulating the at least one second reflector in order to intersect the at least one second reflector with the path for
reflecting the light toward the surface of the test piece while
preventing the lens of the infrared camera from imaging the surface of the test piece; and
heating the surface of the test piece with the light that is redirected by the spatially manipulated at least one second reflector.

17. The method according to claim 16, wherein the spatially manipulating step includes:
oscillating the at least one second reflector for
dynamically changing the reflected direction of the light by the at least one second reflector as the light is being reflected by the at least one second reflector toward the surface of the test piece.

18. The method according to claim 16, further comprising:
after the heating step, further spatially manipulating the at least one second reflector for arranging the at least one second reflector in a position for
preventing the infrared camera from being exposed to heat arising from one or both of the one or more illumination sources and the at least one first reflector; and
permitting the lens of the infrared camera to view the surface of the test piece for imaging the surface of the test piece.

19. The method according to claim 18, further comprising:
processing the imaged surface of the test piece, including converting the image to electronic signals.

20. The method according to claim 19, wherein the processing step includes
applying an adjustment to electronic signals converted from images collected during an extended excitation of the one or more illumination sources by shifting a time assigned to the electronic signals so that at time t=0 indicates a midpoint of a heating period of the surface of the test piece.

21. The method according to claim 20, further including correcting the temperature of the surface of the test piece using:

$$T_{corr}(t) = \frac{T_{raw}(t)}{2\sqrt{t} * \left(\sqrt{t+\frac{\tau}{2}} - \sqrt{t-\frac{\tau}{2}}\right)}$$

22. The method according to claim 20, further including correcting the electronic signals for convection errors using:

$$T(t) = T_{det} e^{ht} - T_{amb}.$$

23. The method according to claim 20, further including collecting the electronic signals for background/emissivity errors using:

$$T(t) = \frac{T_{det} - (1-e)T_{bkgd}}{e}$$

24. The method according to claim 16, wherein the spatially manipulating step includes:
firstly arranging the at least one second reflector in a first position that that does not intersect the path while also preventing the lens of the infrared camera from imaging the surface of the test piece, and
secondly arranging the at least one second reflector in a second position ($\theta_{OPEN}$, $\theta_A$) that that intersects with the path while still preventing the lens of the infrared camera from imaging the surface of the test piece.

25. The method according to claim 16, wherein prior to the directing the light step,
utilizing the infrared camera for acquiring images of the surface of the test piece prior to heating the surface of the test piece.

26. The method according to claim 16, wherein the directing the light step occurs in response to
applying a voltage to the one or more illumination sources; and
only upon determining that a current reaches a threshold level,
raising the voltage and then conducting the spatially manipulating step.

27. The method according to claim 26, wherein, after a period of time,
ceasing the application of the voltage; and
after the heating step, further spatially manipulating the at least one second reflector for arranging the at least one second reflector in a position for
preventing the infrared camera from being exposed to heat arising from one or both of the one or more illumination sources and the at least one first reflector; and
permitting the lens of the infrared camera to view the surface of the test piece for imaging the surface of the test piece.

28. The method according to claim 27 further comprising: processing the imaged surface of the test piece.

29. The method according to claim 28, wherein the processing step includes
applying an adjustment during an extended excitation of the one or more illumination sources by shifting a time assigned to each collected frame produced by the infrared camera so that at time t=0 indicates a midpoint of a heating period of the surface of the test piece.

30. The assembly according to claim 1, wherein the motor is coupled to the at least one second reflector by way of
an axle in order to permit the at least one second reflector to be pivotally adjustable relative to a spatially fixed orientation of the one or more illumination sources and the at least one first reflector.

31. The assembly according to claim 1, wherein the first spatial orientation of the at least one second reflector
does not intersect with a path of the light, wherein the second spatial orientation of the at least one second reflector
intersects with a path of the light.

32. The assembly according to claim 1, wherein the first spatial orientation of the at least one second reflector
intersects with a path of the light, wherein the second spatial orientation of the at least one second reflector intersects with a path of the light.

33. The assembly according to claim 1, wherein the one or more illumination sources includes:
one or more flash lamps that creates a plasma for a few millisecond by an application of a high voltage across a pressurized gas tube.

34. The assembly according to claim 1, wherein the one or more illumination sources includes:
one or more high intensity gas discharge lamps with large filaments.

35. The assembly according to claim 1, wherein the one or more illumination sources includes:
one or more halogen lamps.

36. The assembly according to claim 1, wherein the one or more illumination sources are point filaments that is/are approximately equal to or less than 0.25" that permit closer arrangement of the one or more illumination sources to the near focal point of the at least one first reflector so that the light is focused at the far focal point.

37. The assembly according to claim 1, wherein the at least one first reflector includes an internal reflection surface having an elliptical shape.

38. The assembly according to claim 37, wherein the internal reflection surface includes a polished finish to provide specular reflection.

39. The assembly according to claim 37, wherein the internal reflection surface includes an aluminum coating or a gold coating.

40. The assembly according to claim 1, wherein the at least one first reflector includes an internal reflection surface that is not a parabolic shape.

41. The assembly according to claim 1, wherein the at least one first reflector includes an internal reflection surface that is not a quasi-parabolic shape.

42. The assembly according to claim 1, wherein the system does not include a spectral filter such that the light includes both visible light and infrared light.

43. The assembly according to claim 1, wherein the at least one second reflector is substantially planar.

44. The assembly according to claim 1, wherein the at least one second reflector is slightly curved.

45. The assembly according to claim 1, wherein the at least one second reflector includes a specular reflection surface.

46. The assembly according to claim 1, wherein the at least one second reflector includes a slightly roughened reflection surface.

47. The assembly according to claim 46, wherein the slightly roughened reflection surface is brushed.

48. The assembly according to claim 46, wherein the slightly roughened reflection surface includes patterned aluminum.

49. The assembly according to claim 46, wherein the slightly roughened reflection surface includes patterned gold.

50. An assembly, comprising:
an optically excited infrared nondestructive testing active thermography system including:
one or more illumination sources including:
a first column of illumination sources, and
a second column of illumination sources;
at least one first reflector arranged about each illumination source forming the first column of illumination sources and the second column of illumination sources, wherein the at least one first reflector has a near focal point and a far focal point, wherein the one or more illumination sources is/are positioned at least proximate the near focal point of the at least one first reflector;
at least one second reflector positioned at least proximate the far focal point, wherein the at least one second reflector includes:
a left second reflector, and
a right second reflector, wherein the first column of illumination sources are arranged proximate the left second reflector, wherein the second column of illumination sources are arranged proximate the right second reflector; and
a computing resource communicatively-coupled to a motor that is coupled to the at least one second reflector for manipulating each of the left second reflector and the right second reflector between at least:
a first spatial orientation, and
a second spatial orientation, wherein at least one of the first spatial orientation and the second spatial orientation results in each of the left second reflector and the right second reflector reflecting light that originates from the one or more illumination sources, wherein the light is directed toward each of the left second reflector and the right second reflector as a result of the light being:
directly propagated from the one or more illumination sources, and
reflected by the at least one first reflector.

51. The assembly according to claim 50, wherein the system further includes:
an infrared camera communicatively-coupled to the computing resource, wherein positioning of each of the left second reflector and the right second reflector in the first spatial orientation results in:
the light being substantially directly and indirectly blocked by each of the left second reflector and the right second reflector such that the light is not incident upon or detected by the infrared camera while
the light is reflected by each of the left second reflector and the right second reflector toward a surface of a test piece.

52. The assembly according to claim 51, wherein the system further includes:
an infrared camera communicatively-coupled to the computing resource, wherein positioning of each of the left second reflector and the right second reflector in the second spatial orientation results in:
the infrared camera detecting heat from the surface of the test piece that was heated as a result of the light that was reflected by each of the left second reflector and the right second reflector toward the surface of the test piece while
heat emanating from one or more of the one or more illumination sources and the at least one first reflector is blocked by each of the left second reflector and the right second reflector such that the heat emanating from one or more of the one or more illumination sources and the at least one first reflector is not incident upon or detected by the infrared camera.

53. The assembly according to claim 51, further comprising:
a support structure that is connected to and supports one or more of the one or more illumination sources, the infrared camera, the at least one first reflector, each of the left second reflector and the right second reflector, the computing resource and the motor.

54. The assembly according to claim 53, wherein the support structure includes a housing portion that is connected to and supports the one or more of the one or more illumination sources, the infrared camera, the at least one first reflector, each of the left second reflector and the right second reflector, the computing resource and the motor.

55. The assembly according to claim 54, wherein the housing portion includes:
a plurality of interior walls, and
a plurality of exterior walls, wherein the plurality of interior walls defines a recessed cavity, wherein one or more of the one or more of the one or more illumination sources, the infrared camera, the at least one first reflector, each of the left second reflector and the right second reflector is/are disposed within the recessed cavity.

56. The assembly according to claim 55, further comprising:
a display connected to the computing resource; and
a user interface connected to the computing resource, wherein one or more of the computing resource, the display and the user interface is/are disposed upon one of the plurality of exterior walls of the housing portion.

57. The assembly according to claim 55, wherein the computing resource is a tablet computer, wherein the tablet computer also includes a display and a user interface, wherein the tablet computer is disposed upon one of the plurality of exterior walls of the housing portion.

58. The assembly according to claim 54, wherein the support structure further includes:
a pod portion connected to the housing portion.

59. The assembly according to claim 58, wherein the support structure further includes:
an adjuster portion that connects the housing portion to the pod portion, wherein the adjuster portion permits the housing portion to be pivoted, rotated and/or pitched relative to the pod portion.

60. The assembly according to claim 54, wherein the support structure further includes:
a leg portion connected to the housing portion, and
a linear guide bar connected to one or both of the leg portion and the housing portion, wherein one or more of the leg portion and the linear guide bar includes one or more suction cups to permit one or more of the leg portion and the linear guide bar to be removably-attached to the surface of the test piece.

61. The assembly according to claim 51, wherein the at least one first reflector is arranged relative to the surface of the test piece such that the light is not directed toward the surface of the test piece but rather parallel to the surface of the test piece.

62. The assembly according to claim 51, wherein the system further includes:
an electronic thermometer connected to the computing resource, wherein the electronic thermometer measures ambient air temperature, wherein the computing resource compares the ambient temperature to a detected temperature of the surface of the test piece.

63. The assembly according to claim 50, wherein the motor is coupled, respectively, to each of the left second reflector and the right second reflector by way of
a left axle and a right axle in order to permit each of the left second reflector and the right second reflector to be pivotally adjustable relative to a spatially fixed orientation of the one or more illumination sources and the at least one first reflector.

64. The assembly according to claim 50, wherein the first spatial orientation of each of the left second reflector and the right second reflector
does not intersect with a path of the light, wherein the second spatial orientation of the at least one second reflector
intersects with a path of the light.

65. The assembly according to claim 50, wherein the first spatial orientation of each of the left second reflector and the right second reflector
intersects with a path of the light, wherein the second spatial orientation of each of the left second reflector and the right second reflector
intersects with a path of the light.

66. The assembly according to claim 50, wherein the one or more illumination sources includes:
one or more flash lamps that creates a plasma for a few millisecond by an application of a high voltage across a pressurized gas tube.

67. The assembly according to claim 50, wherein the one or more illumination sources includes:
one or more high intensity gas discharge lamps with large filaments.

68. The assembly according to claim 50, wherein the one or more illumination sources includes:
one or more halogen lamps.

69. The assembly according to claim 50, wherein the one or more illumination sources are point filaments that is/are approximately equal to or less than 0.25" that permit closer arrangement of the one or more illumination sources to the near focal point of the at least one first reflector so that the light is focused at the far focal point.

70. The assembly according to claim 50, wherein the at least one first reflector includes an internal reflection surface having an elliptical shape.

71. The assembly according to claim 70, wherein the internal reflection surface includes a polished finish to provide specular reflection.

72. The assembly according to claim 70, wherein the internal reflection surface includes an aluminum coating or a gold coating.

73. The assembly according to claim 50, wherein the at least one first reflector includes an internal reflection surface that is not a parabolic shape.

74. The assembly according to claim 50, wherein the at least one first reflector includes an internal reflection surface that is not a quasi-parabolic shape.

75. The assembly according to claim 50, wherein the system does not include a spectral filter such that the light includes both visible light and infrared light.

76. The assembly according to claim 50, wherein each of the left second reflector and the right second reflector is substantially planar.

77. The assembly according to claim 50, wherein each of the left second reflector and the right second reflector is slightly curved.

78. The assembly according to claim 50, wherein each of the left second reflector and the right second reflector includes a specular reflection surface.

79. The assembly according to claim 50, wherein each of the left second reflector (20*a*) and the right second reflector includes a slightly roughened reflection surface.

80. The assembly according to claim 79, wherein the slightly roughened reflection surface is brushed.

81. The assembly according to claim 79, wherein the slightly roughened reflection surface includes patterned aluminum.

82. The assembly according to claim 81, wherein the slightly roughened reflection surface includes patterned gold.

* * * * *